(12) United States Patent
Jiang et al.

(10) Patent No.: US 9,701,736 B2
(45) Date of Patent: *Jul. 11, 2017

(54) INFLUENZA HEMAGGLUTININ-SPECIFIC MONOCLONAL ANTIBODIES FOR PREVENTING AND TREATING INFLUENZA VIRUS INFECTION

(71) Applicant: New York Blood Center, Inc., New York, NY (US)

(72) Inventors: Shibo Jiang, New York, NY (US); Lanying Du, Rego Park, NY (US); Yusen Zhou, Beijing (CN)

(73) Assignee: New York Blood Center, Inc., New York, NY (US)

( * ) Notice: Subject to any disclaimer, the term of this patent is extended or adjusted under 35 U.S.C. 154(b) by 2 days.

This patent is subject to a terminal disclaimer.

(21) Appl. No.: 14/511,013

(22) Filed: Oct. 9, 2014

(65) Prior Publication Data

US 2015/0030607 A1 Jan. 29, 2015

Related U.S. Application Data

(63) Continuation of application No. 13/277,515, filed on Oct. 20, 2011, now Pat. No. 8,900,585.

(60) Provisional application No. 61/405,100, filed on Oct. 20, 2010.

(51) Int. Cl.
*C07K 16/10* (2006.01)
*A61K 39/00* (2006.01)

(52) U.S. Cl.
CPC .... *C07K 16/1018* (2013.01); *A61K 2039/505* (2013.01); *C07K 2317/34* (2013.01); *C07K 2317/76* (2013.01)

(58) Field of Classification Search
None
See application file for complete search history.

(56) References Cited

U.S. PATENT DOCUMENTS 8,900,585 B2 * 12/2014 Jiang et al. ............... 424/141.1

FOREIGN PATENT DOCUMENTS

| SG | WO 2009/035420 | * | 3/2009 | ............ C07K 16/10 |
| WO | 2008/036675 A2 | | 3/2008 | |
| WO | 2008/140415 A1 | | 11/2008 | |

OTHER PUBLICATIONS

Khurana et al. (PLoS Medicine, Apr. 2009, vol. 6, p. 1-13).*
Owens et al. (Journal of Immunological Methods, 1994).*
Bottje et al., XP-002666748 Sequence 21 from EP2066339.
Bottje et al., XP-002666749 Sequence 22 from EP2066339.
Churchill et al., Crystal structure of a peptide complex of anti-influenza peptide antibody Fab 26/9. Comparison of two different antibodies bound to the same peptide antigen. J. Mol. Bioi., 241:534-556 (1994).
H5N1 HA-1 protein PubMed 2013.
International Search Report mailed on Jan. 18, 2012 for International Application No. PCT/US2011/057127 filed on Oct. 20, 2011.
Khurana et al., Antigenic fingerprinting of H5N1 avian influenza using convalescent sera and monoclonal antibodies reveals potential vaccine and diagnostic targets. PLoS Medicine, vol. 6, Issue 4, e1000049 (2009).
Wang et al, Generating and characterizing monoclonal and polyclonal antibodies against avian H5N1 hemagglutinin protein. Biochem. Biophys. Res. Comm., 382:691-696 (2009).
Simmons CP et al. "Prophylactic and therapeutic efficacy of human monoclonal antibodies against H5N1 influenza," PLoS Medicine 4:e178, 2007.

* cited by examiner

*Primary Examiner* — Agnieszka Boesen
(74) *Attorney, Agent, or Firm* — K&L Gates LLP; Louis C. Cullman; Michelle Glasky Bergman

(57) ABSTRACT

Disclosed herein are neutralizing antibodies with cross-neutralizing activity and cross-protective effects against divergent stains of influenza virus, which are specific for an epitope having at least 90% homology to amino acids +72-115 of the HA1 domain of H5N1 influenza virus hemagglutinin.

6 Claims, 13 Drawing Sheets

FIG. 6

Legend:
- HA-3: 10 μg/ml
- HA-3: 0.7 μg/ml
- HA-7: 10 μg/ml
- HA-7: 0.7 μg/ml

Y-axis: % Neutralization
X-axis: H5N1 pseudoviruses (XJ-HA, QH-HA, AH-HA, HK-HA, 1194-HA)

FIG. 7

Legend:
- HA-3
- HA-7
- Control

Y-axis: Mouse survival rate (%)
X-axis: Days post infection

*Mouse body weight (%)* vs *Days post infection*

- HA-3
- HA-7
- Control

*Viral titers ($Log_{10} TCID_{50}/g$)*

- HA-3
- HA-7
- Control

VN/1194, SZ/406H

H5N1 virus infection

INFLUENZA HEMAGGLUTININ-SPECIFIC MONOCLONAL ANTIBODIES FOR PREVENTING AND TREATING INFLUENZA VIRUS INFECTION

CROSS-REFERENCE TO RELATED APPLICATIONS

This application is a continuation of U.S. patent application Ser. No. 13/277,515 filed Oct. 20, 2011, which claims the benefit under 35 U.S.C. §119(e) to U.S. Provisional Patent Application 61/405,100 filed Oct. 20, 2010, the entire contents of both of which are incorporated by reference herein.

FIELD

The present application is drawn to neutralizing monoclonal antibodies for preventing and treating influenza virus infection and methods of treating influenza virus infection.

BACKGROUND

The Influenza A virus, which belongs to the Orthomyxoviridae family, can cause influenza in humans, birds or domesticated food animals. The virus can be classified into different subtypes based on their surface glycoproteins, hemagglutinin (HA) and neuraminidase (NA). Of the 16 known HAs and nine NAs, three HA subtypes (H1, H2, and H3) and two NA subtypes (N1 and N2) are most commonly found in humans. H1N1 and H3N2 are the major subtypes that cause human seasonal flu and global pandemics of influenza. The influenza pandemic in 2009 was caused by influenza A virus H1N1 of swine origin. This has led to a growing concern regarding the pandemic potential of the highly pathogenic avian influenza H5N1 viruses. Thus the development of an effective and safe vaccine against divergent influenza A virus strains is urgently needed for the prevention of future outbreaks of influenza.

Neutralizing monoclonal antibodies (MAbs), particularly those having cross-clade neutralizing activity, play a critical role in immunoprotection against various influenza A virus (IAV) infections, particularly those caused by the highly pathogenic avian influenza H5N1 virus and any future unpredictable virus strains.

Although vaccination is an important strategy to prevent influenza infection, most of the current vaccines cannot provide immediate protection in the event of influenza pandemics and epidemics due to the length of time required for producing effective vaccines. Furthermore, these vaccines are limited to one or just a few strains and don't produce highly potent neutralizing antibodies or cross-reactive immunity against divergent influenza viruses. Neutralizing antibodies can provide a first line of defense against influenza pathogens and passive immunization with neutralizing MAbs can provide immediate effects to prevent the spread of influenza infection and mortality. However, it has been difficult to obtain MAbs which neutralize divergent strains of influenza viruses with sufficient cross-protective immunity.

SUMMARY

Disclosed herein are neutralizing monoclonal antibodies (MAbs) specific for the surface hemagglutinin (HA) protein of the influenza H5N1 strain. The MAbs recognize the highly conserved HA1 region of H5N1 hemagglutinin and inhibit multiple strains of the H5N1 virus, as well as treated mice infected with a lethal dose of H5N1 viruses of two divergent strains, demonstrating their potential as therapeutic agents for multivalent prophylaxis and treatment of influenza. These two MAbs were proven to inhibit virus infection in the post-attachment process rather than inhibition of receptor binding.

In one embodiment disclosed herein, a neutralizing antibody specific for an epitope having at least 90% homology to amino acids +72-115 of the HA1 domain of H5N1 influenza virus hemagglutinin is provided. In another embodiment, the neutralizing antibody is a monoclonal antibody such as a mouse antibody, a humanized antibody, a chimeric antibody, or a fragment thereof.

In another embodiment, the epitope has at least 95% or at least 98% homology to amino acids +72-115 of the HA1 domain of H5N1 influenza virus hemagglutinin.

In yet another embodiment, the neutralizing antibody is produced by hybridoma HA-3 (ATCC accession number PTA-12174). In yet another embodiment, the neutralizing antibody is produced by hybridoma HA-7 (ATCC accession number PTA-12173). Hybridomas HA-3 and HA-7 were deposited with the American Type Culture Collection (ATCC), 10801 University Blvd., Manassas, Va. 20110 under the provisions of the Budapest Treaty.

Also disclosed herein is a pharmaceutical formulation for neutralizing influenza virus comprising an antibody specific for an epitope having at least 90% homology to amino acids +72-115 of the HA1 domain of H5N1 influenza virus hemagglutinin.

Also disclosed herein is a method of treating influenza virus infection in a subject in need thereof comprising administering a therapeutically effective amount of the neutralizing antibody specific for an epitope having at least 90% homology to amino acids +72-115 of the HA1 domain of H5N1 influenza virus hemagglutinin and thereby treating said influenza virus infection in said subject.

BRIEF DESCRIPTION OF THE DRAWINGS

FIG. 6 depicts the percentage of neutralization by MAbs HA-3 and HA-7 at two concentrations of H5N1 pseudovirus expressing HA of five different strains, as measured by pseudovirus neutralization assay.

FIG. 7 depicts the survival rate of MAbs HA-3- and HA-7-treated mice infected with a lethal dose of A/Viet- Nam/1194/2004 (VN/1194) H5N1 virus. The control mice were treated with a MAb targeting the receptor-binding domain (RBD) of severe acute respiratory syndrome coronavirus (SARS-CoV).

FIG. 10 depicts the body weight change of MAbs HA-3- and HA-7-treated mice infected with lethal dose of SZ/406H H5N1 virus. A MAb targeting the RBD of SARS-CoV was used as the control.

FIG. 11 depicts the quantification of viral RNA in H5N1 virus-infected lung tissue of mice injected with MAbs HA-3 and HA-7 by quantitative real-time PCR. A MAb targeting the RBD of SARS-CoV was used as the control. The limit of detection was 1.5.

FIG. 15 depicts epitope mapping of the MAbs HA-3 and HA-7, as measured by ELISA on plates coated with truncated recombinant HA1 protein fragments comprising the indicated portions of the HA1 region. The dilution of the antibody was 1:3200.

FIG. 16A-C depicts the reactivity of MAbs HA-3 and HA-7 with different overlapping peptides covering the full-length HA protein of A/Anhui/1/2005(H5N1), as measured by ELISA. The dilution of the antibody was 1:3200.

FIG. 19 depicts the binding of MAb HA-3 to H5N1 pseudovirus, as measured by post-attachment assay using QH-HA pseudovirus in virus-infected MDCK cells.

FIG. 20 depicts the binding of MAb HA-7 to H5N1 pseudovirus, as measured by post-attachment assay using QH-HA pseudovirus in virus-infected MDCK cells.

DETAILED DESCRIPTION

Figure 1:
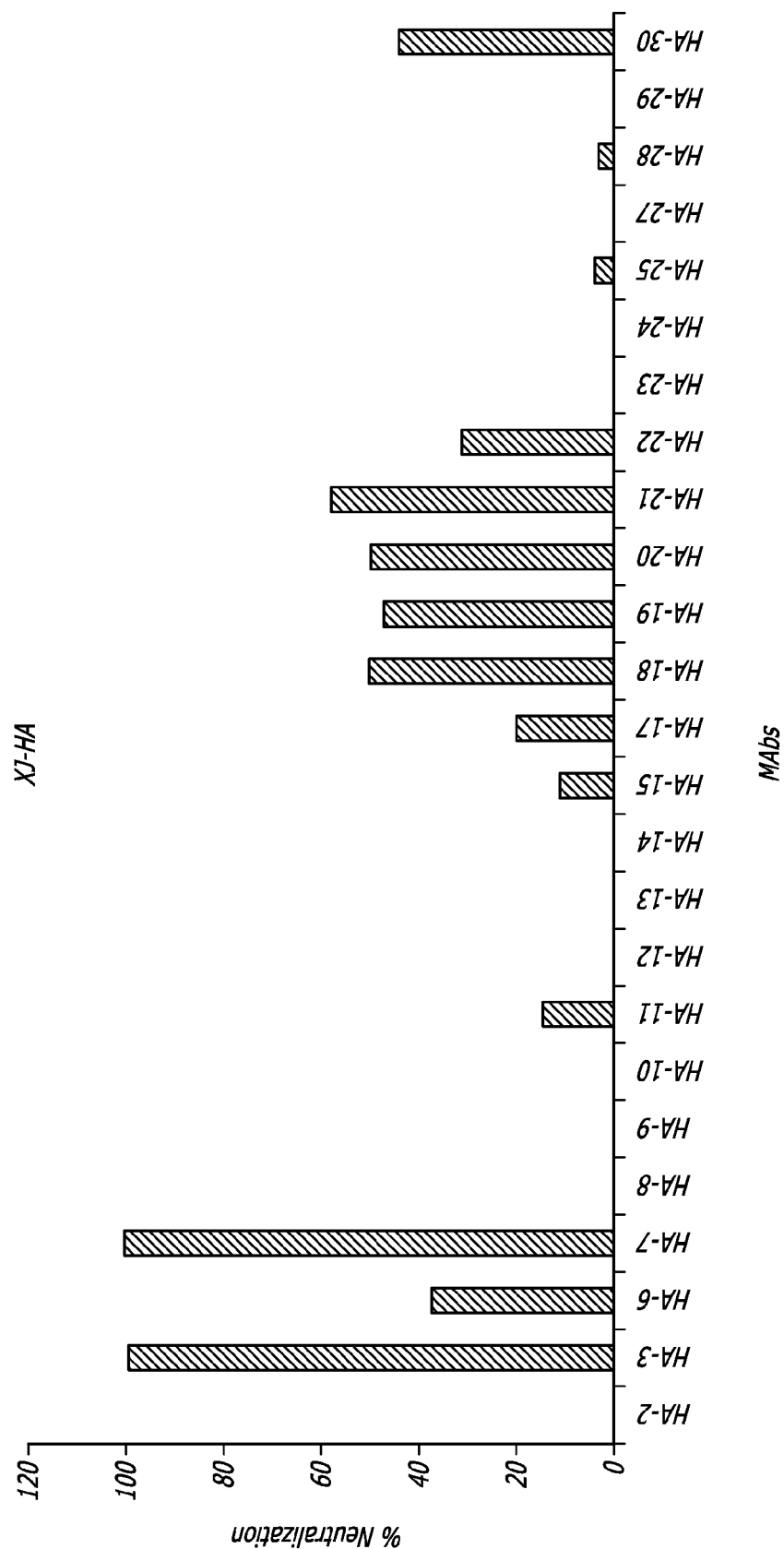
FIG. 1 depicts the percentage of neutralization by HA-targeting MAbs of H5N1 pseudovirus expressing HA of A/Xinjiang/1/2006 (XJ-HA), as measured by pseudovirus neutralization assay. The dilution of the MAbs is 1:450.
Figure 2:
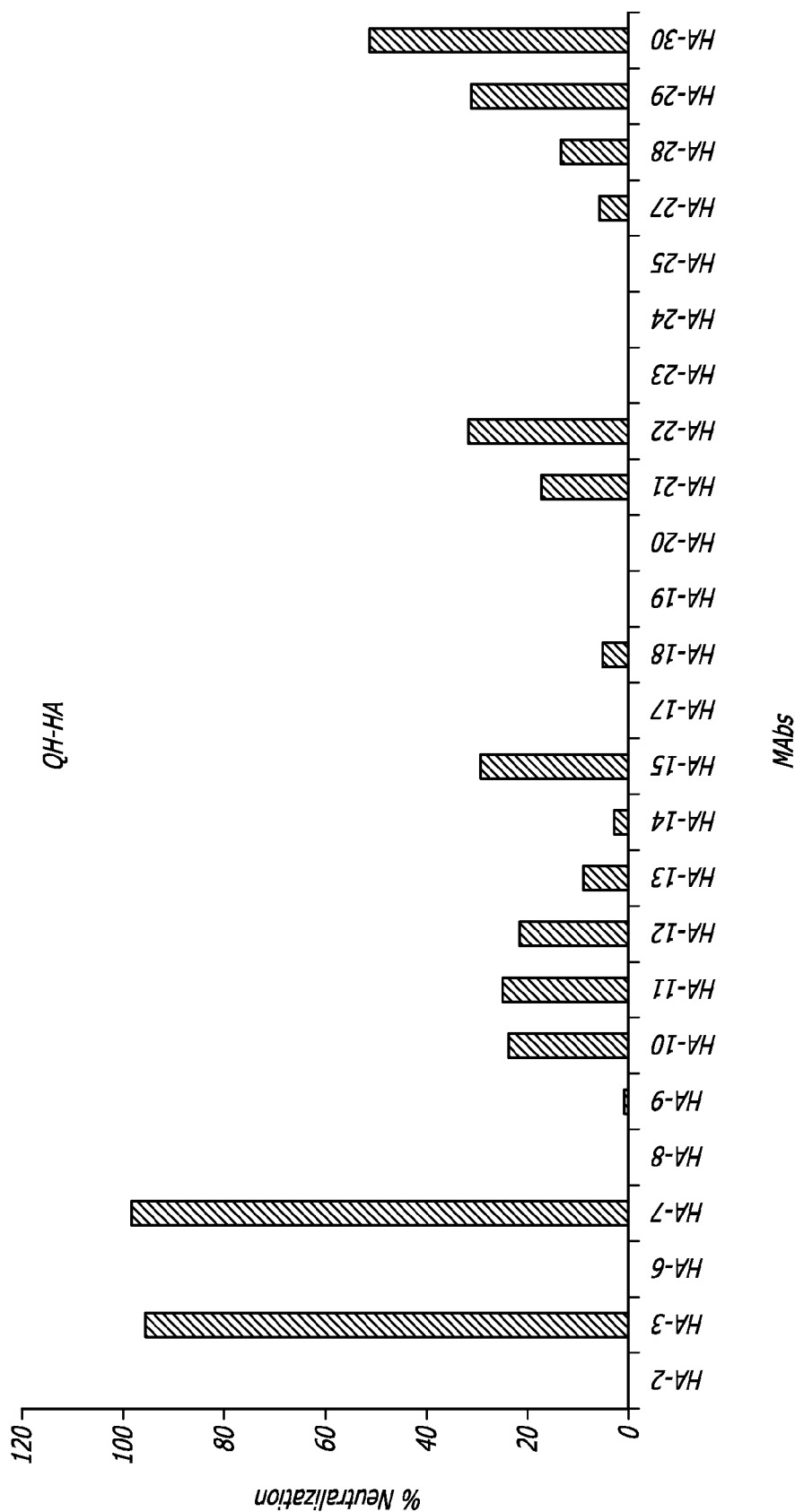
FIG. 2 depicts the percentage of neutralization by HA-targeting MAbs of H5N1 pseudovirus expressing A/Qinghai/59/05 (QH-HA), as measured by pseudovirus neutralization assay. The dilution of the MAbs is 1:450.
Figure 3:
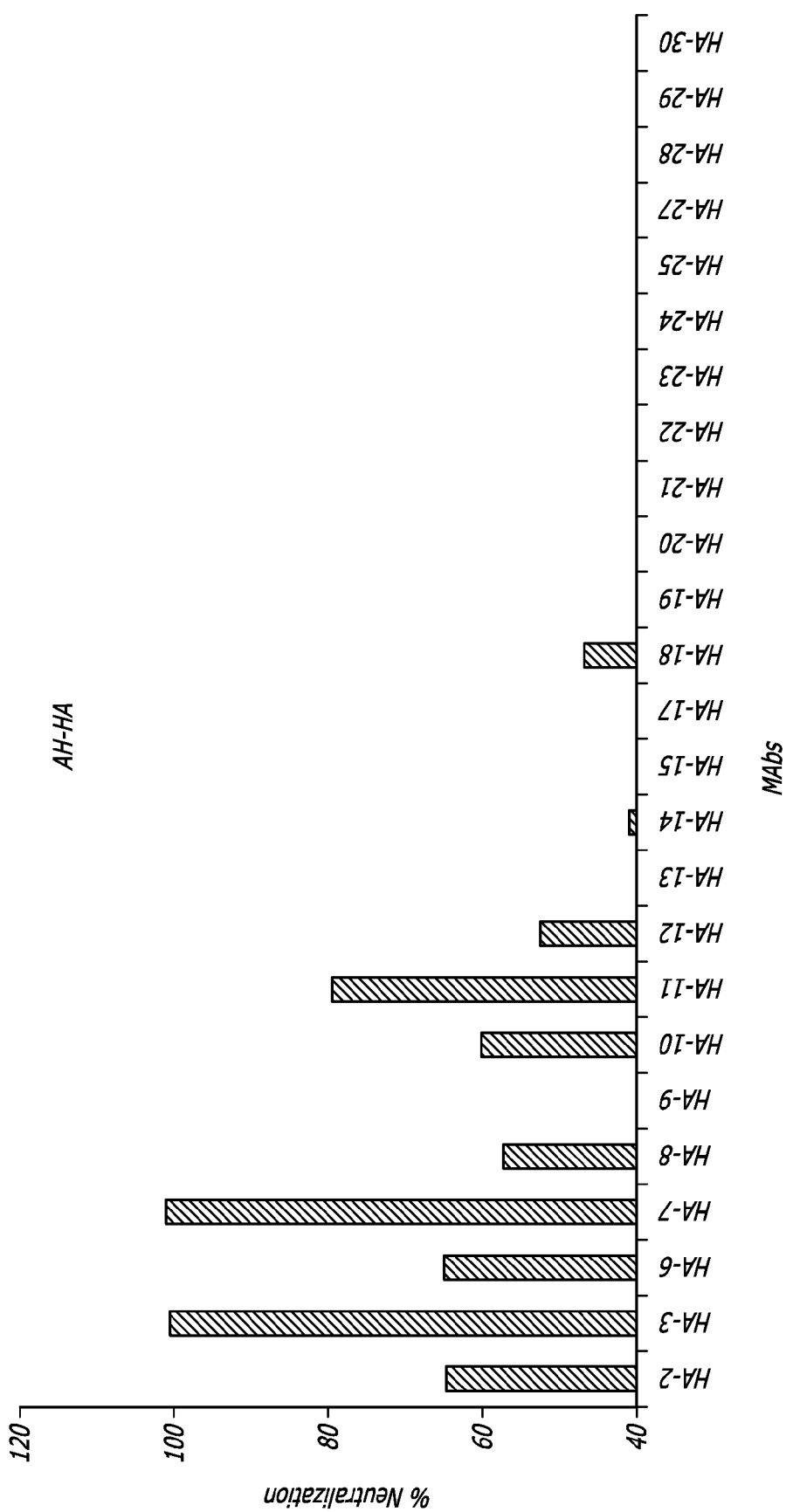
FIG. 3 depicts the percentage of neutralization by HA-targeting MAbs of H5N1 pseudovirus expressing HA of A/Anhui/1/2005 (AH-HA), as measured by pseudovirus neutralization assay. The dilution of the MAbs is 1:450.
Figure 4:
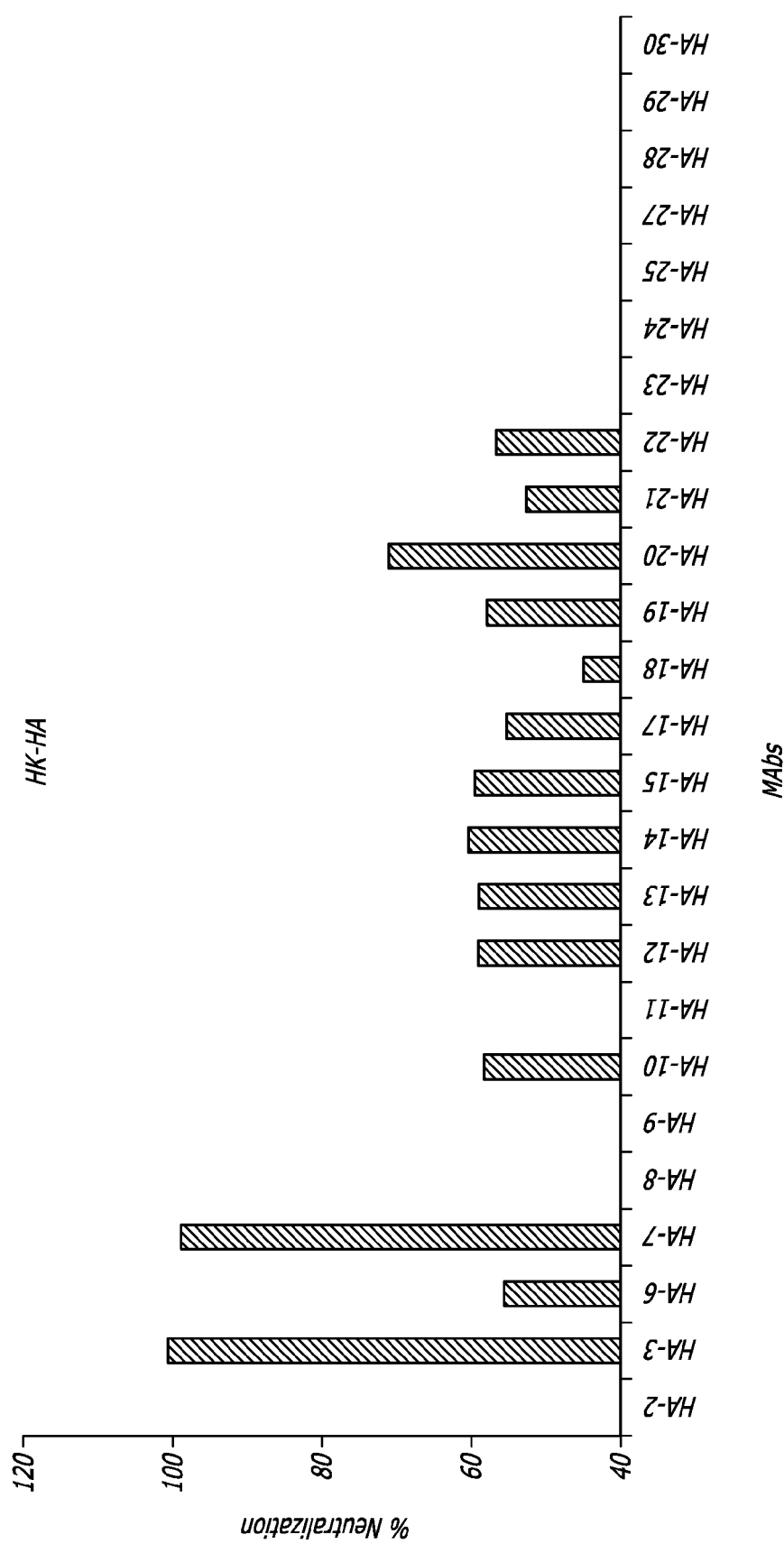
FIG. 4 depicts the percentage of neutralization by HA-targeting MAbs of H5N1 pseudovirus expressing HA of A/Hong Kong/156/97 (HK-HA), as measured by pseudovirus neutralization assay. The dilution of the MAbs is 1:450.
Figure 5:
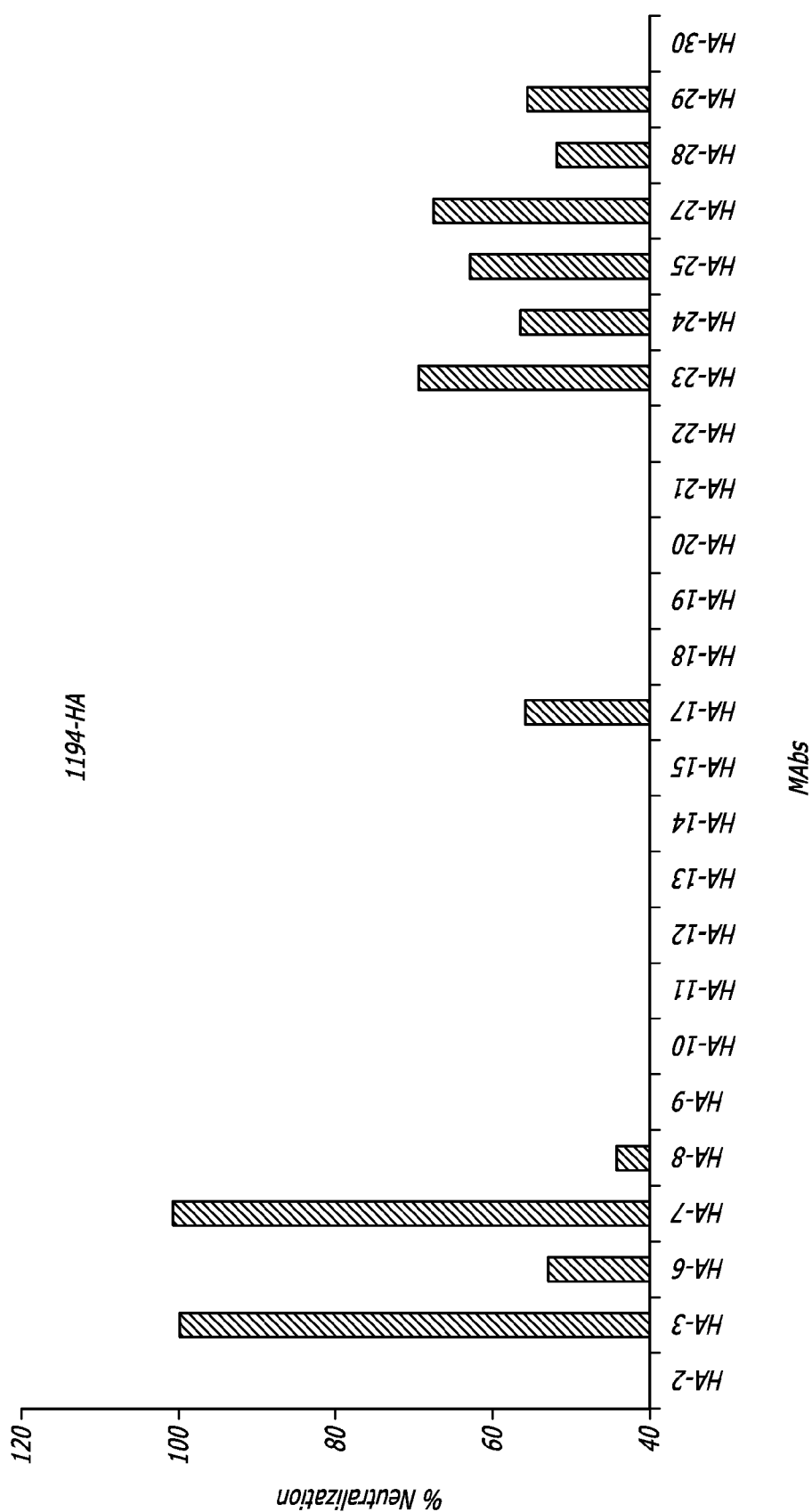
FIG. 5 depicts the percentage of neutralization by HA-targeting MAbs of H5N1 pseudovirus expressing HA of A/VietNam/1194/2004 (1194-HA), as measured by pseudovirus neutralization assay. The dilution of the MAbs is 1:450.

Development of universal neutralizing monoclonal antibodies (MAbs) with cross-protective immunity is crucial to prevent and treat influenza pandemics and epidemics caused by divergent strains of influenza A virus (IAV). Disclosed herein are protective neutralizing MAbs specific to the hemagglutinin (HA) protein (SEQ ID NO. 1) of the H5N1 virus produced by immunizing mice with a recombinant protein encoding HA1 (SEQ ID NO. 2) of the A/Anhui/1/2005 (H5N1) strain fused with the trimeric motif foldon (Fd) (SEQ ID NO. 3) and the Fc portion of human IgG1 (SEQ ID NO. 4). Two of these MAbs (HA-3 and HA-7) have highly potent cross-neutralizing activity that neutralized infections with at least five strains of H5N1 pseudovirus expressing HA proteins, including homologous A/Anhui/1/2005 (AH-HA) and heterologous A/Xinjiang/1/2006 (XJ-HA), A/Qinghai/59/05 (QH-HA), A/Hong Kong/156/97 (HK-HA) and A/VietNam/1194/2004 (1194-HA) in a cell culture-based neutralization assay. ELISA-based epitope mapping analysis indicated that the neutralizing MAbs targeted the N-terminal of the HA1 region of H5N1 HA, a highly conserved region with >90% homology among hundreds of identified H5N1 isolates that cause human and non-human infections. These results indicate that the MAbs are potentially significant immunotherapeutics for prevention or treatment of IAV infections, particularly those caused by the highly pathogenic H5N1 virus.

Annually-occurring epidemics and pandemics caused by IAVs have claimed millions of lives worldwide. This has been seen most recently in the global outbreak of swine-origin influenza virus (S-OIV) H1N1 in 2009. Furthermore, the increasing number of influenza cases caused by the highly pathogenic avian influenza virus H5N1 makes it particularly important to develop effective preventative and immunotherapeutic measures against divergent IAVs, particularly avian H5N1. Among various antiviral agents, neutralizing MAbs are considered an essential passive immunotherapeutic having an immediate effect against influenza virus infection. Disclosed herein are two novel neutralizing MAbs targeting the highly conserved HA1 region of the HA protein of H5N1.

In embodiments disclosed herein, the HA sequences refer to HA or HA1 sequences of the following influenza viruses H5N1, H1N1, H3N2, H9N2 and the H1, H2, H3, H5, H7 and H9 strains.

Additionally, within the scope of the instant disclosure are chimeric, or antibody fragments with specificity for the epitope having 80%, 85%, 90%, 92%, 95%, 97%, 98%, 99% or 100% homology to amino acids +72-115 (SEQ ID NO. 15) of the influenza H5N1 virus HA1 domain and having virus neutralizing activity. In one embodiment, the monoclonal antibodies are antibodies HA-3 (produced by hybridoma HA-3 having ATCC accession number PTA-12174) and HA-7 (produced by hybridoma HA-7 having ATCC accession number PTA-12173). Hybridomas HA-3 and HA-7 were deposited with the American Type Culture Collection (ATCC), 10801 University Blvd., Manassas, Va. 20110 under the provisions of the Budapest Treaty.

TABLE 1

Amino acid sequences

SEQ ID NO. 1 [A/Anhui/1/2005(H5N1) HA]:
MEKIVLLLAIVSLVKSDQICIGYHANNSTEQVDTIMEKNVTVTHAQDILEKTHNGKLCDLDGVK
PLILRDCSVAGWLLGNPMCDEFINVPEWSYIVEKANPANDLCYPGNFNDYEELKHLLSRINHFE
KIQIIPKSSWSDHEASSGVSSACPYQGTPSFFRNVVWLIKKNNTYPTIKRSYNNTNQEDLLILW TABLE 1-continued Amino acid sequences GIHHSNDAAEQTKLYQNPTTYISVGTSTLNQRLVPKIATRSKVNGQNGRMDFFWTILKPNDAIN
FESNGNFIAPEYAYKIVKKGDSAIVKSEVEYGNCNTKCQTPIGAINSSMPFHNIHPLTIGECPK
YVKSNKLVLATGLRNSPLRERRRKRGLFGAIAGFIEGGWQGMVDGVVYGYHHSNEQGSGYAADK
ESTQKAIDGVTNKVNSIIDKMNTQFEAVGREFNNLERRIENLNKKMEDGFLDVWTYNAELLVLM
ENERTLDFHDSNVKNLYDKVRLQLRDNAKELGNGCFEFYHKCDNECMESVRNGTYDYPQYSEEA
RLKREEISGVKLESIGTYQILSIYSTVASSLALAIMVAGLSLWMCSNGSLQCRICI SEQ ID NO. 2 [A/Anhui/1/2005(H5N1) HA1 +3-322]:
ICIGYHANNST TABLE 1-continued Amino acid sequences VSSACPYQGTPSFFRNVVWLIKKNNTYPTIKRSYNNTNQEDLLILWGIHHSNDAAEQTKLYQNP
TTYISVGTSTLNQRLVPKIATRSKVNGQNGRMDFFWTILKPNDAINFESNGNFIAPEYAYKIVK
K SEQ ID NO. 12 [A/Anhui/1/2005(H5N1) HA1 +28-259]:
HAQDILEKTHNGKLCDLDGVKPLILRDCSVAGWLLGNPMCDEFINVPEWSYIVEKANPANDLCY
PGNFNDYEELKHLLSRINHFEKIQIIPKSSWSDHEASSGVSSACPYQGTPSFFRNVVWLIKKNN
TYPTIKRSYNNTNQEDLLILWGIHHSNDAAEQTKLYQNPTTYISVGTSTLNQRLVPKIATRSKV
NGQNGRMDFFWTILKPNDAINFESNGNFIAPEYAYKIVKK SEQ ID NO. 13 [A/Anhui/1/2005(H5N1) HA1 +45-259]:
DGVKPLILRDCSVAGWLLGNPMCDEFINVPEWSYIVEKANPANDLCYPGNFNDYEELKHLLSRI
NHFEKIQIIPKSSWSDHEASSGVSSACPYQGTPSFFRNVVWLIKKNNTYPTIKRSYNNTNQEDL
LILWGIHHSNDAAEQTKLYQNPTTYISVGTSTLNQRLVPKIATRSKVNGQNGRMDFFWTILKPN
DAINFESNGNFIAPEYAYKIVKK SEQ ID NO. 14 [A/Anhui/1/2005(H5N1) HA1 +72-259]:
NVPEWSYIVEKANPANDLCYPGNFNDYEELKHLLSRINHFEKIQIIPKSSWSDHEASSGVSSAC
PYQGTPSFFRNVVWLIKKNNTYPTIKRSYNNTNQEDLLILWGIHHSNDAAEQTKLYQNPTTYIS
VGTSTLNQRLVPKIATRSKVNGQNGRMDFFWTILKPNDAINFESNGNFIAPEYAYKIVKK SEQ ID NO. 15 [A/Anhui/1/2005(H5N1) HA1 +72-115]:
NVPEWSYIVEKANPANDLCYPGNFNDYEELKHLLSRINHFEKIQ SEQ ID NO. 16 [A/Anhui/1/2005(H5N1) HA1(+105-322)-Fd-hFc]:
LSRINHFEKIQIIPKSSWSDHEASSGVSSACPYQGTPSFFRNVVWLIKKNNTYPTIKRSYNNTN
QEDLLILWGIHHSNDAAEQTKLYQNPTTYISVGTSTLNQRLVPKIATRSKVNGQNGRMDFFWTI
LKPNDAINFESNGNFIAPEYAYKIVKKGDSAIVKSEVEYGNCNTKCQTPIGAINSSMPFHNIHP
LTIGECPKYVKSNKLVLATGLRNSPL-GYIPEAPRDGQAYVRKDGEWVLLSTFL-RSDKTHTCP
PCPAPELLGGPSVFLFPPKPKDTLMISRTPEVTCVVVDVSHEDPEVKFNVVYVDGVEVHNAKTK
PREEQYNSTYRVVSVLTVLHQDWLNGKEYKCKVSNKALPAPIEKTISKAKGQPREPQVYTLPPS
REEMTKNQVSLTCLVKGFYPSDIAVEWESNGQPENNYKTTPPVLDSDGSFFLYSKLTVDKSRWQ
QGNVFSCSVMHEALHNHYTQKSLSLSPGK SEQ ID NO. 17 [A/Anhui/1/2005(H5N1) HA1(+105-259)-Fd-hFc]:
LSRINHFEKIQIIPKSSWSDHEASSGVSSACPYQGTPSFFRNVVWLIKKNNTYPTIKRSYNNTN
QEDLLILWGIHHSNDAAEQTKLYQNPTTYISVGTSTLNQRLVPKIATRSKVNGQNGRMDFFWTI
LKPNDAINFESNGNFIAPEYAYKIVKK-GYIPEAPRDGEVVLLSTFL-RSDKTHT
CPPCPAPELLGGPSVFLFPPKPKDTLMISRTPEVTCVVVDVSHEDPEVKFNWYVDGVEVHNAKT
KPREEQYNSTYRVVSVLTVLHQDWLNGKEYKCKVSNKALPAPIEKTISKAKGQPREPQVYTLPP
SREEMTKNQVSLTCLVKGFYPSDIAVEWESNGQPENNYKTTPPVLDSDGSFFLYSKLTVDKSRW
QQGNVFSCSVMHEALHNHYTQKSLSLSPGK SEQ ID NO. 18 [A/Anhui/1/2005(H5N1) HA1(+3-259)-Fd-hFc]:
ICIGYHANNSTEQVDTIMEKNVTVTHAQDILEKTHNGKLCDLDGVKPLILRDCSVAGWLLGNPM
CDEFINVPEWSYIVEKANPANDLCYPGNFNDYEELKHLLSRINHFEKIQIIPKSSWSDHEASSG
VSSACPYQGTPSFFRNVVWLIKKNNTYPTIKRSYNNTNQEDLLILWGIHHSNDAAEQTKLYQNP
TTYISVGTSTLNQRLVPKIATRSKVNGQNGRMDFFWTILKPNDAINFESNGNFIAPEYAYKIVK
K-GYIPEAPRDGQAYVRKDGEVVLLSTFL-RSDKTHTCPPCPAPELLGGPSVFLFPPKPKDTL
MISRTPEVTCVVVDVSHEDPEVKFNVVYVDGVEVHNAKTKPREEQYNSTYRVVSVLTVLHQDWL
NGKEYKCKVSNKALPAPIEKTISKAKGQPREPQVYTLPPSREEMTKNQVSLTCLVKGFYPSDIA
VEWESNGQPENNYKTTPPVLDSDGSFFLYSKLTVDKSRWQQGNVFSCSVMHEALHNHYTQKSLS
LSPGK SEQ ID NO. 19 [A/Anhui/1/2005(H5N1) HA1(+28-259)-Fd-hFc]:
HAQDILEKTHNGKLCDLDGVKPLILRDCSVAGWLLGNPMCDEFINVPEWSYIVEKANPANDLCY
PGNFNDYEELKHLLSRINHFEKIQIIPKSSWSDHEASSGVSSACPYQGTPSFFRNVVWLIKKNN
TYPTIKRSYNNTNQEDLLILWGIHHSNDAAEQTKLYQNPTTYISVGTSTLNQRLVPKIATRSKV
NGQNGRMDFFWTILKPNDAINFESNGNFIAPEYAYKIVKK-GYIPEAPRDGQAYVRKDGEWVLL
STFL-RSDKTHTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEKTISKAKG
QPREPQVYTLPPSREEMTKNQVSLTCLVKGFYPSDIAVEWESNGQPENNYKTTPPVLDSDGSFF
LYSKLTVDKSRWQQGNVFSCSVMHEALHNHYTQKSLSLSPGK SEQ ID NO. 20 [A/Anhui/1/2005(H5N1) HA1(+45-259)-Fd-hFc]:
DGVKPLILRDCSVAGWLLGNPMCDEFINVPEWSYIVEKANPANDLCYPGNFNDYEELKHLLSRI
NHFEKIQIIPKSSWSDHEASSGVSSACPYQGTPSFFRNVVWLIKKNNTYPTIKRSYNNTNQEDL
LILWGIHHSNDAAEQTKLYQNPTTYISVGTSTLNQRLVPKIATRSKVNGQNGRMDFFWTILKPN
DAINFESNGNFIAPEYAYKIVKK-GYIPEAPRDGQAYVRKDGEVVLLSTFL-RSDKTHTCPPC
PAPELLGGPSVFLFPPKPKDTLMISRTPEVTCVVVDVSHEDPEVKFNVVYVDGVEVHNAKTKPR
EEQYNSTYRVVSVLTVLHQDWLNGKEYKCKVSNKALPAPIEKTISKAKGQPREPQVYTLPPSRE
EMTKNQVSLTCLVKGFYPSDIAVEWESNGQPENNYKTTPPVLDSDGSFFLYSKLTVDKSRWQQG
NVFSCSVMHEALHNHYTQKSLSLSPGK SEQ ID NO. 21 [A/Anhui/1/2005(H5N1) HA1(+72-259)-Fd-hFc]:
NVPEWSYIVEKANPANDLCYPGNFNDYEELKHLLSRINHFEKIQIIPKSSWSDHEASSGVSSAC
PYQGTPSFFRNVVWLIKKNNTYPTIKRSYNNTNQEDLLILWGIHHSNDAAEQTKLYQNPTTYIS
VGTSTLNQRLVPKIATRSKVNGQNGRMDFFWTILKPNDAINFESNGNFIAPEYAYKIVKK-GYI

TABLE 1-continued

Amino acid sequences

PEAPRDGQAYVRKDGEVVVLLSTFL-RSDKTHTCPPCPAPELLGGPSVFLFPPKPKDTLMISRT
PEVTCVVVDVSHEDPEVKFNVVYVDGVEVHNAKTKPREEQYNSTYRVVSVLTVLHQDWLNGKEY
KCKVSNKALPAPIEKTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNHYTQKSLSLSPGK

SEQ ID NO. 22 [A/Anhui/1/2005(H5N1) HA1(+72-115)-Fd-hFc]:
NVPEWSYIVEKANPANDLCYPGNFNDYEELKHLLSRINHFEK1Q-GYIPEAPRDGQAYVRKDGE
VVVLLSTFL-RSDKTHTCPPCPAPELLGGPSVFLFPPKPKDTLMISRTPEVTCVVVDVSHEDPE
VKFNWYVDGVEVHNAKTKPREEQYNSTYRVVSVLTVLHQDWLNGKEYKCKVSNKALPAPIEKTI
SKAKGQPREPQVYTLPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGK For the generation of MAbs specific to HA1, BALB/c mice were subcutaneously immunized with a recombinant HA1-Fd-hFc protein (SEQ ID NO. 5) which comprised HA1 (residues +3-322 of H5N1 HA [A/Anhui/1/2005(H5N1)]) fused with a trimeric Fd sequence and an Fc immunoenhancer sequence (Fc of human IgG) for four weeks at 2 week intervals. Two MAbs exhibiting neutralizing activity (HA-3 and HA-7) were tested for passive protective immunity against two divergent strains of H5N1 virus. In addition, the MAbs were assayed by ELISA for specificity using recombinant HA1 proteins fused with Fd and hFc (HA1-Fd-hFc), Fd (HA1-Fd), hFc (HA1-hFc) or HA1 without Fd and Fc (HA1-His), and using recombinant human IgG1-Fc (hFc), commercial human IgG-Fc (IgG-Fc), Fd protein fused with HIV-gp41 (HIV-Fd), or SARS RBD protein as controls. These two MAbs were further tested by ELISA for reactivity with recombinant proteins containing different portions of the HA1 fusion protein (HA1-Fd-hFc) to determine the potential binding sites and map the epitopes of the MAbs. Furthermore, overlapping peptides covering the full-length HA protein of A/Anhui/1/2005(H5N1) were also used as the targets for the epitope mapping of the MAbs, as well as detection of the conformation of the MAbs. Additionally, the mechanism of these two neutralizing MAbs was further analyzed using virus binding and post-attachment assays.

Two of the 25 antibodies, designated HA-3 and HA-7, contained high titers of neutralizing activity that neutralized not only the homologous AH-HA strain but also heterologous H5N1 strains of XJ-HA, QH-HA, HK-HA and 1194-HA. Both MAbs were able to completely protect vaccinated mice against two H5N1 live viruses of divergent strains. The above results demonstrate that these two antibodies are effective against divergent strains of IAVs. In addition, epitope analysis indicated that these MAbs exhibited strong reactivity against recombinant HA1 fusion proteins containing residues +3-322 (SEQ ID NO. 2), +3-259 (SEQ ID NO. 11), +28-259 (SEQ ID NO. 12), +45-259 (SEQ ID NO. 13), +72-259 (SEQ ID NO. 14), as well as +72-115 (SEQ ID NO. 15), but had little to no reactivity against protein fragments covering residues +105-322 (SEQ ID NO. 9) and +105-259 (SEQ ID NO. 10). These results indicate that the neutralizing activity may be mapped to residues +72-115 of H5N1 HA1. Amino acid sequence alignment of the HA1 region indicates that the +72-115 region is highly conserved (>90% homology) among hundreds of strains of H5N1 viruses causing human and non-human influenza infections, implying that the identified neutralizing MAbs recognized a highly conserved region of IAV HA1. These results also demonstrated that the identified neutralizing MAbs had very low to no reactivity with overlapping peptides covering the full-length HA indicated by low $OD_{450}$ values detected by ELISA. The overlapping peptides have been known to be of a linear structure, without forming the native conformation of the HA structure. In contrast, recombinant proteins expressing different HA1 fragments of H5N1 virus fused with Fd and Fc, which were used for the above antibody reactivity detection, maintain the native trimeric structure of the HA protein. However, when the conformation of these HA1 fusion proteins were destroyed by denaturing reagent, such as DTT, their reactivity with the two MAbs was decreased to a large extent. Thus, the fact that the MAbs had strong reactivity with native recombinant HA1 proteins but low to no reactivity with DTT-treated denatured HA proteins or overlapping peptides covering this region suggests that the identified neutralizing MAbs recognized conformational structures similar to the native HA proteins of H5N1 virus.

Furthermore, the results demonstrated that both neutralizing MAbs (HA-3 and HA-7) reacted strongly with HA1 proteins fused with the immunoenhancer Fc of human IgG1 (HA1-hFc) (SEQ ID NO. 6), trimeric motif foldon (Fd) sequences (HA1-Fd) (SEQ ID NO. 7), Fd plus Fc (HA1-Fd-hFc) (SEQ ID NO. 5) or HA1 protein alone (HA1-His) (SEQ ID NO. 8), but only background or no reactivity with recombinant Fc of human IgG1 (hFc) (SEQ ID NO. 4), commercial human IgG (IgG-Fc), Fd control protein fused with HIV gp41 (HIV-Fd) and a control protein comprised of the receptor binding domain (RBD) of SARS-CoV (SARS RBD), indicating that the neutralizing MAbs are highly specific to the HA1 protein of H5N1. This is in part due to the highly selective screening regimen (HA1-His protein without Fd and Fc and inactivated H5N1 virus). Further experimentation determined that both neutralizing antibodies are of the IgG1 subtype.

Further embodiments within the scope of this disclosure include methods of preventing or treating influenza infections comprising administering a therapeutically-effective or prophylactically effective amount of a monoclonal antibody having specificity for an epitope having at least 90%, at least 92%, at least 95%, at least 97%, at least 98%, or at least 99% homology to amino acids +72-115 of the HA1 domain of H5N1 influenza virus hemagglutinin.

A pharmaceutical composition comprising the antibodies disclosed herein includes an acceptable carrier and is formulated into a suitable dosage form according to administration modes. Pharmaceutical preparations suitable for administration modes are known, and generally include surfactants that facilitate transport across the membrane. Such surfactants may be derived from steroids, or may be cationic lipids such as N-[1-(2,3-dioleyloxyl)propyl]-N,N, N-trimethylammonium chloride (DOTMA), or various compounds such as cholesterol hemisuccinate and phosphatidyl glycerol.

For oral administration, the pharmaceutical composition may be presented as discrete units, for example, capsules or tablets; powders or granules; solutions, syrups or suspensions (edible foam or whip formulations in aqueous or non-aqueous liquids); or emulsions.

For parenteral administration, the pharmaceutical composition may include aqueous and non-aqueous sterile injection solutions which may contain anti-oxidants, buffers, bacteriostats and solutes which render the formulation substantially isotonic with the blood of the intended recipient; and aqueous and non-aqueous sterile suspensions which may include suspending agents and thickening agents. Excipients available for use in injectable solutions include, for example, water, alcohol, polyols, glycerin, and vegetable oils. Such a composition may be presented in unit-dose (single dose) or multiple dose (several doses) containers, for example, sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

The pharmaceutical composition may include antiseptics, solubilizers, stabilizers, wetting agents, emulsifiers, sweeteners, colorants, odorants, salts, buffering agents, coating agents, or anti-oxidants.

If desired, the present composition, in addition to the antibody or antibodies, may contain a therapeutically active agent.

The present composition may be formulated into dosage forms for use in humans or veterinary use.

In still another aspect, disclosed herein is a method of treating influenza by administering the aforementioned antibodie(s).

The composition comprising the antibodie(s) may be administered to influenza-infected or highly susceptible humans and livestock, such as cows, horses, sheep, swine, goats, camels, and antelopes, in order to prevent or treat the incidence of influenza. When a subject is already infected, the present antibody(s) may be administered alone or in combination with another antiviral treatment.

The antibody composition may be administered in a pharmaceutically effective amount in a single- or multiple-dose. The pharmaceutical composition may be administered via any of the common routes, as long as it is able to reach the desired tissue. Thus, the present composition may be administered via oral or parenteral (e.g., subcutaneous, intramuscular, intravenous, or intradermal administration) routes, and may be formulated into various dosage forms. In one embodiment, the formulation is an injectable preparation. Intravenous, subcutaneous, intradermal, intramuscular and dropping injectable preparations are possible.

The antibody composition may be administered in a pharmaceutically effective amount. The term "pharmaceutically effective amount", as used herein, refers to an amount sufficient for treating or preventing diseases, which is commensurate with a reasonable benefit/risk ratio applicable for medical treatment or prevention. An effective dosage amount of the composition may be determined depending on the severity of the illness, drug activity, the patient's age, weight, health state, gender and drug sensitivity, administration routes, drugs used in combination with the composition; and other factors known in medicine, and may be readily determined by those skilled in the art. The antibody composition may be administered as a sole therapeutic agent or in combination with other therapeutic agents, and may be administered sequentially or simultaneously with conventional therapeutic agents. This administration may be provided in single or multiple doses.

EXAMPLES

Example 1

Generation of Monoclonal Antibodies

For the generation of MAbs specific to HA1, BALB/c mice were subcutaneously immunized with a recombinant HA1-Fd-hFc protein (SEQ ID NO. 5) which comprised HA1 (residues +3-322 of H5N1 HA [A/Anhui/1/2005(H5N1)]) (SEQ ID NO. 2) fused with a trimeric Fd sequence (SEQ ID NO. 3) and an Fc immunoenhancer sequence (Fc of human IgG, hFc) (SEQ ID NO. 4) for four weeks at two week intervals. Three days after the last vaccination, the mice were sacrificed and the splenocytes fused with mouse myeloma cells (SP2/0). The hybridomas were screened by ELISA against an HA1-His protein (SEQ ID NO. 8) which comprised the same HA1 region as the immunogen but was not fused to Fd or hFc. Clones which had positive results against HA1-His were also screened against inactivated H5N1 virus of the homologous Anhui strain. Clones positive in both ELISA assays were then expanded, retested and subcloned to generate stable hybridoma cell lines. Twenty-five MAbs with high titer antibody responses were then screened for neutralizing activity against influenza virus in a pseudovirus neutralization assay including HA proteins of various isolates of influenza A viruses. The MAbs exhibiting neutralizing activity (HA-3 and HA-7) were then tested for passive protective immunity against two divergent strains of H5N1 virus. In addition, the MAbs were assayed by ELISA for specificity using recombinant HA1 proteins, or SARS RBD protein as controls. These two MAbs were further tested by ELISA for reactivity with recombinant proteins containing different portions of the HA1 fusion protein (HA1-Fd-hFc) to determine the potential binding sites and map the epitopes of the MAbs. Furthermore, overlapping peptides covering the full-length HA protein of A/Anhui/1/2005(H5N1) were also used as the targets for the epitope mapping of the MAbs, as well as detection of the conformation of the MAbs. At last, the mechanism of these two neutralizing MAbs was further analyzed using virus binding assay and post-attachment assay.

Example 2

Virus Neutralization Assay and Protective Effects

Monoclonal antibodies (MAbs) HA-2, HA-3, HA-6, HA-7, HA-8, HA-9, HA-10, HA-11, HA-12, HA-13, HA-14, HA-15, HA-17, HA-18, HA-19, HA-20, HA-21, HA-22, HA-23, HA-24, HA-25, HA-27, HA-28, HA-29 and HA-30 were tested in this assay.

An equal volume of H5N1 pseudovirus was added to wells containing the MAbs above and the plates incubated for 1 hr at 37° C. One hundred microliters of the virus/MAb mixture was then added to 293T cells plated 6-8 hr previously. Fifty microliters fresh FBS-DMEM medium was added 24 hr later and then luciferase activity was detected 72 hr later. H5N1 pseudoviruses used for the test include XJ-HA, QH-HA, AH-HA, HK-HA, and 1194-HA.

The protective potential of HA-3 and HA-7 MAbs against H5N1 influenza virus infection was detected in mice. Six to eight week old female BALB/c mice were infected with 5 $LD_{50}$ (50% lethal dose) of A/VietNam/1194/2004 (VN/1194, clade 1) or A/Shenzhen/406H/06 (SZ/406H, clade 2.3.4) H5N1 virus. Twenty-four hours later, the mice were intravenously (i.v.) injected with 0.5 ml of purified MAbs containing 1 mg of HA-3 or HA-7. The control group was given same amount of a MAb specific to the RBD protein of SARS-CoV. Six infected mice per group were observed daily for 14 days to calculate the survival rate and body weight change. Six mice from each group were sacrificed on day 5 post-treatment, and lung samples were collected for virological detection.

A total of 25 MAbs selected from the fusion of HA1-Fd-hFc protein-immunized mouse splenocytes were screened for neutralizing activity by the pseudovirus H5N1 neutralization assay. Two antibodies (HA-3 and HA-7) exhibited high titers of neutralizing activity that not only neutralized the homologous AH-HA strain but also neutralized heterologous XJ-HA, QH-HA, HK-HA and 1194-HA strains (FIGS. 1-5). Importantly, both HA-3 and HA-7 were able to neutralize over 95% of the H5N1 pseudoviruses, including XJ-HA, QH-HA, AH-HA and HK-HA, at the concentration as low as 0.7 μg/ml (FIG. 6).

Figure 8:
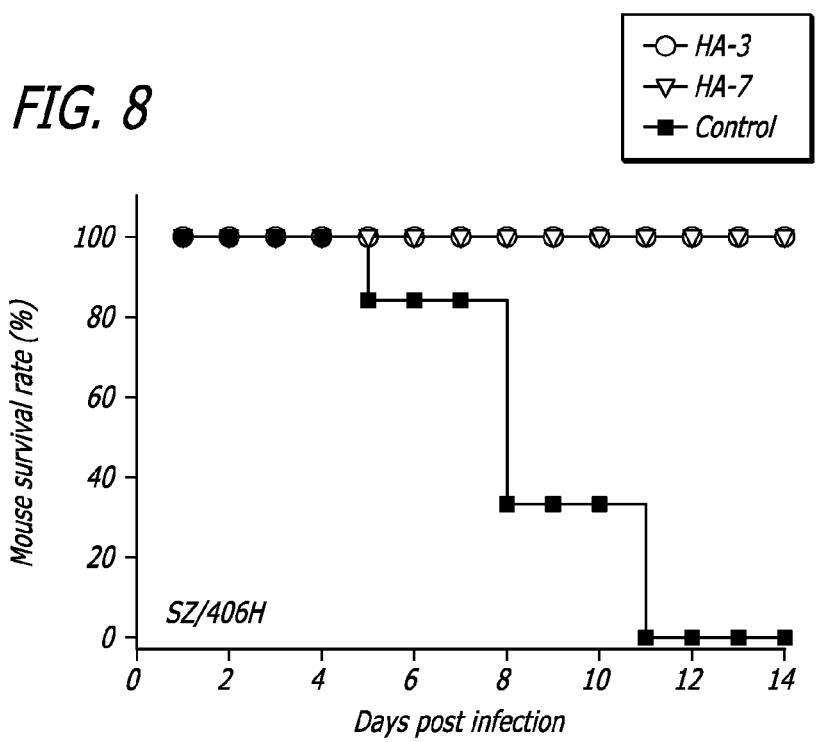
FIG. 8 depicts the survival rate of MAbs HA-3- and HA-7-treated mice infected with a lethal dose of A/Shenzhen/406H/06 (SZ/406H) H5N1 virus. A MAb targeting the RBD of SARS-CoV was used as the control.
Figure 9:
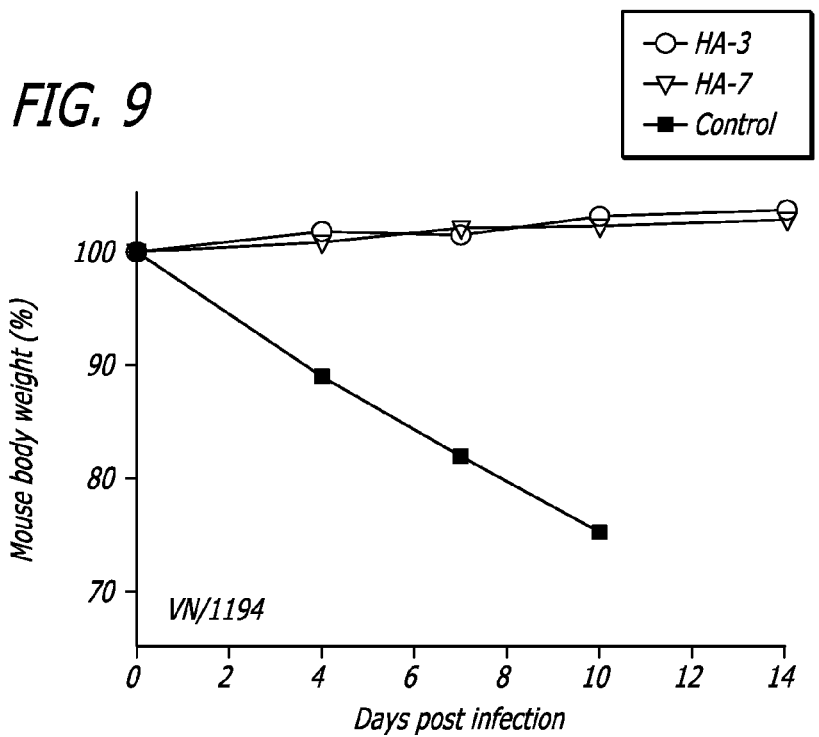
FIG. 9 depicts the body weight change of MAbs HA-3- and HA-7-treated mice infected with lethal dose of VN/1194 H5N1 virus. A MAb targeting the RBD of SARS-CoV was used as the control.

All mice injected with HA-3 and HA-7 MAbs survived the infection with VN/1194 (clade 1) (FIG. 7) and SZ/406H (clade 2.3.4) (FIG. 8) H5N1 virus, while no mice from the control group (injected with MAb against RBD of SARS-CoV) survived infection with the above two viruses. In addition, no obvious body weight loss was observed in the mice immunized with HA-3 and HA-7 MAbs after infection with a lethal dose of VN/1194 (FIG. 9) or SZ/406H (FIG. 10) H5N1 virus, while the mice in the control group indicated continuous decrease of body weight, and none of them survived for over 10 days after infection with the virus. Observation of the viral titers in the infected mouse lung tissues indicated that no viral RNA was detectable in both HA-3 and HA-7-treated mice infected with VN/1194 and SZ/406H viruses, while a high level of viral RNA was detected in the control mice injected with the MAb specific to the RBD of SARS-CoV (FIG. 11). These results demonstrate that the two identified neutralizing MAbs HA-3 and HA-7 completely treated mice against lethal infection with clade 1 and clade 2.3.4 strains of H5N1 virus, indicating their use as passive immunotherapy for H5N1 virus infection.

Example 3

Specificity Detection and IgG Subtyping

ELISA plates were coated with the following purified proteins at a concentration of 1 μg/ml at 50 μl/well in 0.1 M carbonate buffer (pH 9.6): HA1-Fd-hFc (SEQ ID NO. 5), HA1-hFc (SEQ ID NO. 6), HA1-Fd (SEQ ID NO. 7), HA1-His (SEQ ID NO. 8), recombinant hIgG1-Fc2 protein (hFc) (SEQ ID NO. 4), commercial human IgG Fc protein (IgG-Fc) and foldon (Fd) fused with HIV-1 gp41 (HIV-Fd), as well as SARS RBD protein as controls. The plates were stored at 4° C. overnight to coat. The coated plates were then blocked using 2% nonfat milk in phosphate-buffered saline/Tween (PBST) for 2 hr at 37° C. The MAb-containing supernatants were diluted in sample buffer (1% nonfat milk) and incubated with the coated plates at 50 μl/well for 1 hr at 37° C. The plates were then washed three times in PBST. Goat anti-mouse IgG HRP (1:2000), IgG1 HRP (1:2000), IgG2a HRP (1:5000), IgG2b HRP (1:2000) was added at 50 μl/well for 1 hr at 37° C. For IgG3 detection, a goat anti-mouse IgG3 (1:1000) was added at 50 μl/well for 1 hr at 37° C., the plates were washed and then anti-goat HRP (1:5000) was added at 50 μl/well for 1 hr at 37° C. The plates were washed again and 50 μl/well 3,3',5,5'-tetramethylbenzidine (TMB) was added, followed by 25 μl/well 1N $H_2SO_4$ to stop the reaction.

Figure 12:
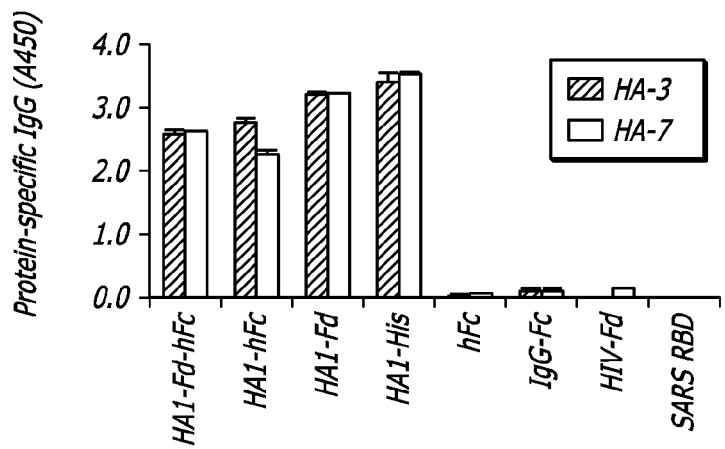
FIG. 12 depicts the ELISA detection of the reactivity of MAbs HA-3 and HA-7 with recombinant HA1 proteins respectively fused with the human Fc immunoenhancer (HA1-hFc), trimeric Fd sequences (HA1-Fd), or the Fd plus hFc (HA1-Fd-hFc), and HA1 protein without the hFc and Fd (HA1-His), as well as recombinant hIgG1-Fc2 protein (hFc), commercial human IgG Fc protein (IgG-Fc), Fd fused with HIV-1 gp41 (HIV-Fd), and SARS RBD protein. The dilution of the antibody was 1:3200.
Figure 13:
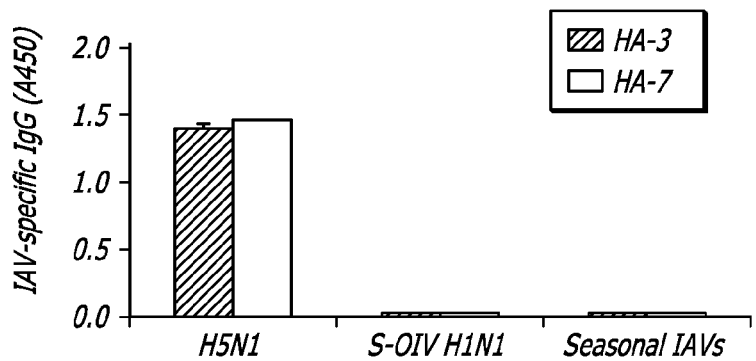
FIG. 13 depicts the reactivity of MAbs HA-3 and HA-7 with inactivated influenza A viruses (IAVs), as measured by ELISA. The dilution of the antibody was 1:3200.
Figure 14:
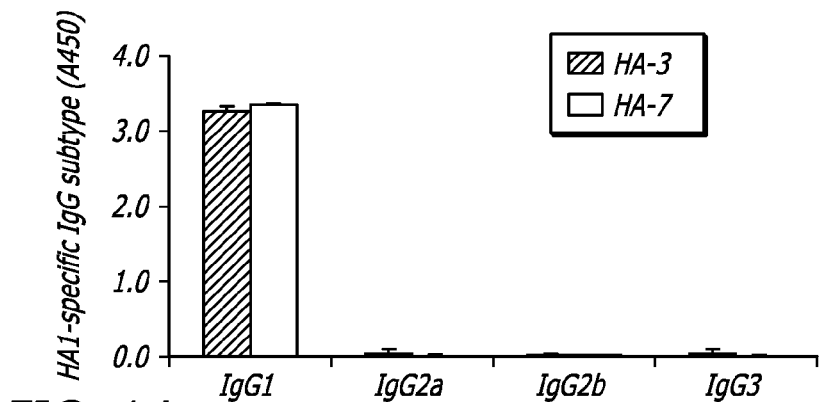
FIG. 14 depicts the detection of IgG subtypes of MAbs HA-3 and HA-7, as measured by ELISA, using recombinant HA1-His protein as the coating antigen. The dilution of the antibody was 1:3200.

Both neutralizing MAbs (HA-3 and HA-7) reacted strongly with recombinant HA1 proteins fused with the hFc (IgG1) immunoenhancer (HA1-hFc) (SEQ ID NO. 6), the trimeric Fd sequences (HA1-Fd), or the Fd plus hFc (HA1-Fd-hFc), and HA1 protein without the hFc and Fd (HA1-His), but only background levels of immunoreactivity were seen with hFc, IgG-Fc and the recombinant control proteins HIV-Fd and SARS RBD (FIG. 12). In addition, these two MAbs had strong reactivity with inactivated H5N1 virus, but low to no reactivity with 2009 swine-origin influenza A virus (S-OIV) H1N1 and 2009/2010 seasonal influenza virus strains consisting of H1N1, H3N2 influenza A virus, and influenza B virus (FIG. 13). The above results indicate that the selected MAbs are highly specific to the HA1 protein of H5N1 virus. Both neutralizing MAbs were determined to be IgG1 subtype (FIG. 14).

Example 4

Epitope Mapping

ELISA plates were coated with the following purified truncated HA1 protein fragments at a concentration of 1 μg/ml at 50 μl/well in 0.1 M carbonate buffer (pH 9.6): HA+3-322 (HA1-Fd-hFc) (SEQ ID NO. 5), HA+105-322 (SEQ ID NO. 9), HA+105-259 (SEQ ID NO. 10), HA+3-259 (HA-3-259) (SEQ ID NO. 11), HA+28-259 (SEQ ID NO. 12), HA+45-259 (SEQ ID NO. 13), HA+72-259 (SEQ ID NO. 14) and HA+72-115 (SEQ ID NO. 15). The plates were stored at 4° C. overnight to coat. The coated plates were then blocked using 2% nonfat milk in PBST for 2 hr at 37° C. The MAb-containing supernatants were diluted in sample buffer (1% nonfat milk) and incubated with the coated plates at 50 μl/well for 1 hr at 37° C. The plates were then washed three times in PBST. Goat anti-mouse horseradish peroxidase (HRP) at 1:2000 dilution was added at 50 μl/well for 1 hr at 37° C. The plates were washed again and 50 μl/well TMB was added, followed by 25 μl/well 1N $H_2SO_4$ to stop the reaction.

Figures 15, 16A:
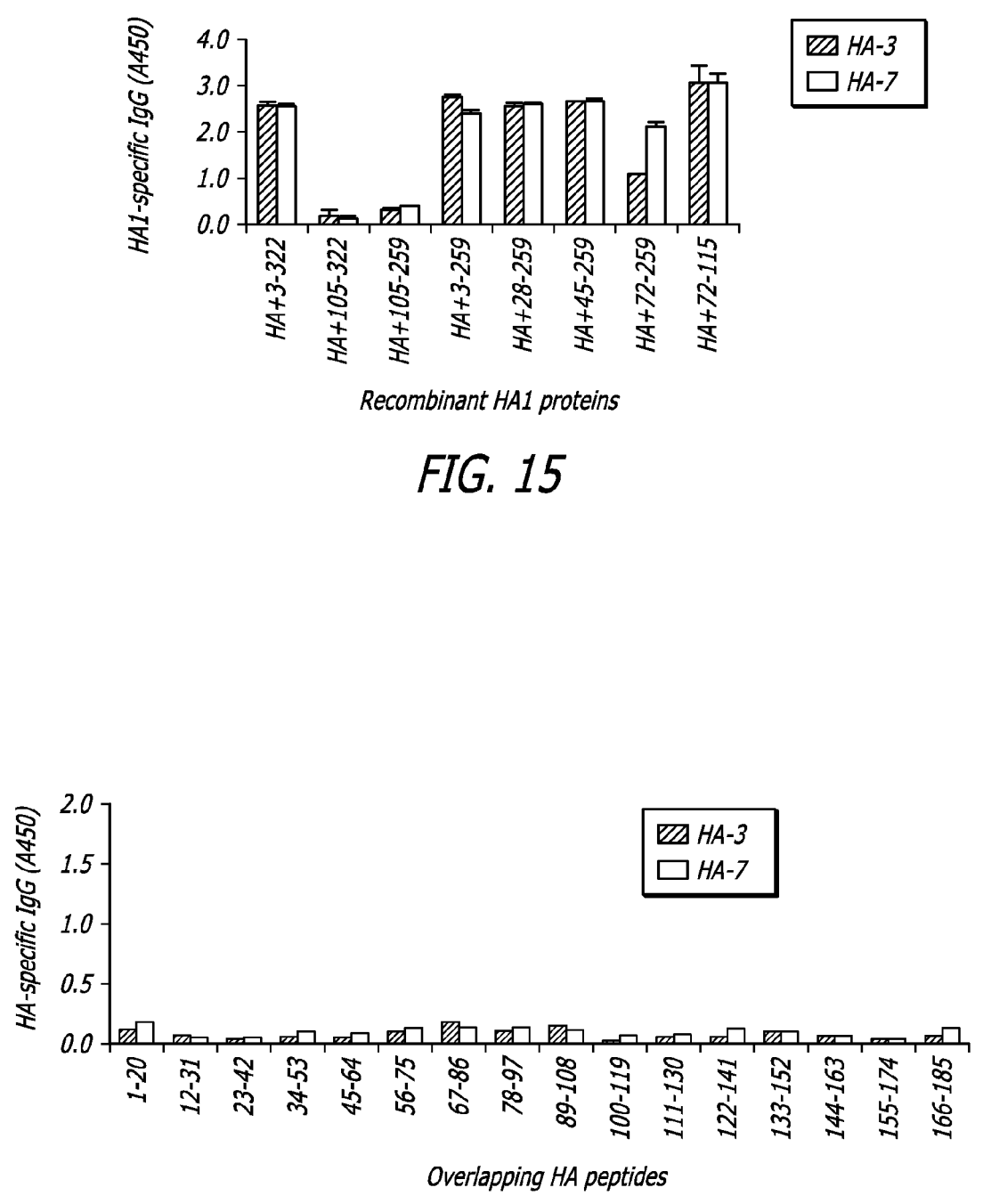

The ELISA data indicated that the two neutralizing MAbs (HA-3 and HA-7) reacted strongly with proteins covering the full-length HA1 of +3-322, and truncated HA1 fragments of +3-259, +28-259, +45-259, +72-259 and +72-115. However, these two MAbs had low to no reactivity with proteins containing HA+105-322 and HA+105-259 (FIG. 15). These results suggest that the two neutralizing antibodies are specific for an epitope mapped to amino acids +72-115 (NVPEWSYIVEKANPANDLCYPGNFN DYEELKHLLSRINHFEKIQ, SEQ ID NO:15) of the HA1 region of H5N1.

Analysis of the epitope amino acid sequences indicated that the residues +72-115 region are highly conserved (>90% homology) among hundreds of strains of H5N1 viruses covering different clades that cause human and non-human influenza infections.

The above HA1 proteins (SEQ ID NO. 5 and SEQ ID NO. 16-22) used for coating the ELISA plates were expressed in mammalian 293T cells and were fused with the foldon (Fd) trimeric sequence and human IgG1 Fc immunoenhancer, such that the proteins have the ability to maintain the native conformational structure of the HA protein. Therefore the two neutralizing MAbs can recognize the native conformation of the HA proteins.

Example 5

Reactivity to Overlapping Peptides and Denatured HA1 Fusion Proteins

ELISA plates were coated overnight at 4° C. with overlapping peptides (20 residues each overlapping 9 amino acid) covering the full-length HA protein (SEQ ID NO. 1) of A/Anhui/1/2005(H5N1) at a concentration of 10 µg/ml at 50 µl/well in 0.1 M carbonate buffer (pH 9.6), and then blocked using 2% nonfat milk in PBST for 2 hr at 37° C. The MAbs were added to the coated plates at 50 µl/well for 1 hr at 37° C. The plates were then washed three times in PBST. Goat anti-mouse HRP (1:2000) was added at 50 µl/well for 1 hr at 37° C. The plates were washed again and 50 µl/well TMB was added, followed by 25 µl/well 1N $H_2SO_4$ to stop the reaction.

To detect the reactivity of MAbs HA-3 and HA-7 with denatured HA1 proteins, ELISA plates were coated with recombinant HA1 proteins at 1 µg/m overnight at 4° C. Then the coated plates were treated with DTT (final concentration 10 mM) for 1 hr at 37° C., followed by washes with PBST. Then the wells were treated with 50 mM iodoacetamide for 1 hr at 37° C. After washing with PBST, ELISA was performed as above.

Figure 16B:
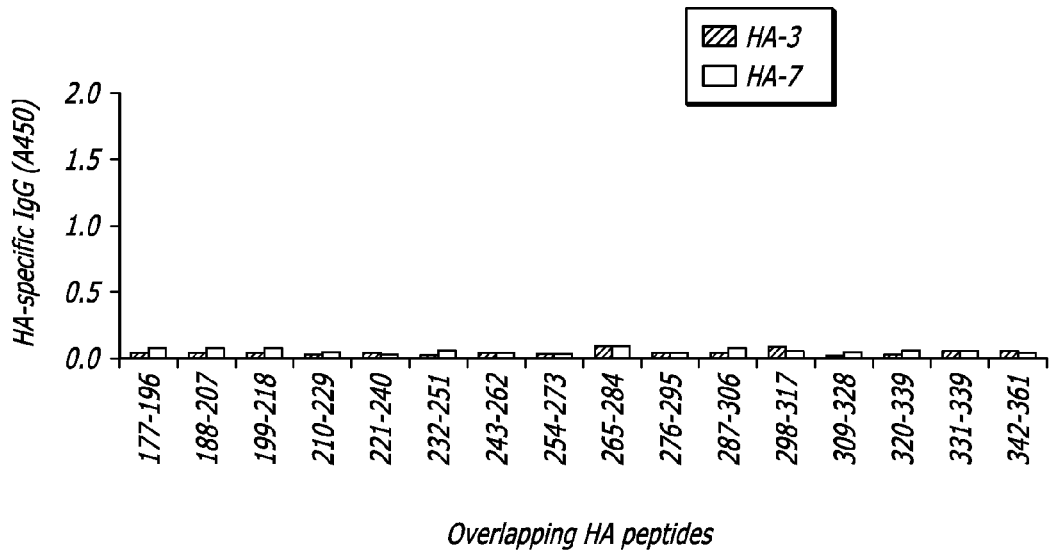
Figure 16C:
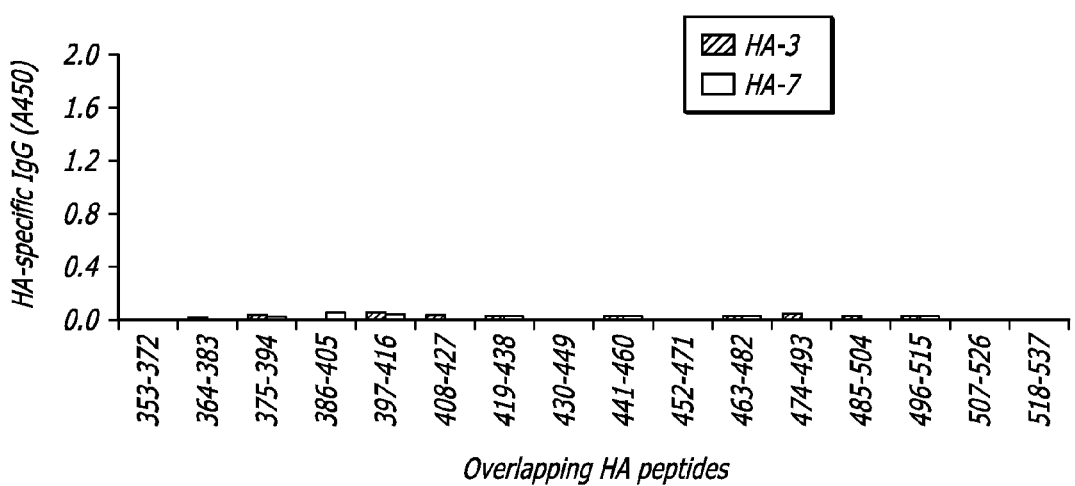
Figure 17:
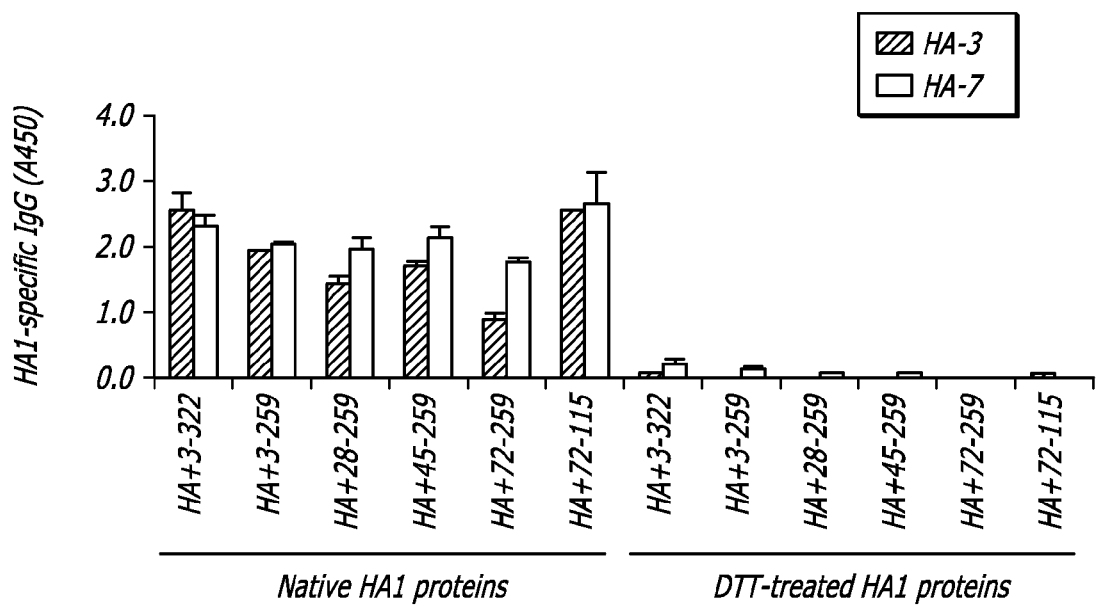
FIG. 17 depicts the reactivity of MAbs HA-3 and HA-7 with DTT-denatured recombinant HA1 proteins of different lengths, with the native HA1 proteins without DTT treatment as a comparison. The dilution of the antibody was 1:51200.

Neutralizing MAbs HA-3 and HA-7 had very low reactivity with overlapping peptides covering the full-length HA proteins of H5N1 (FIGS. 16A-C). These peptides were linear and did not form the native three-dimensional conformation of the HA structure. Similarly, the reactivity of MAbs HA-3 and HA-7 with DTT-treated HA1 fusion proteins decreased significantly, although these MAbs have strong reactivity with native forms of HA1 proteins (FIG. 17).

The fact that MAbs HA-3 and HA-7 had a strong reaction with recombinant proteins encompassing different fragments (covering +72-115 amino acids) of the HA1 of H5N1 with Fd and Fc (FIG. 17) but have little to no reactivity with denatured HA1 proteins (FIG. 17) or overlapping peptides covering this region (FIG. 16) indicates that the identified neutralizing MAbs recognize conformational structures similar to native HA proteins rather than linear structures.

Example 6

Mechanism of Inhibition by MAbs

Virus binding assays were performed using the QH-HA H5N1 pseudovirus. The virus was incubated with serial diluted MAbs HA-3 and HA-7 or IgG-Fc control antibody in DMEM containing 1% BSA at 4° C. overnight. MDCK cells were seeded in 96-well plates 24 hr before infection and blocked with DMEM containing 1% BSA (100 µl/well) at 4° C. for 1 hr. The mixture of virus and MAbs was then added to MDCK cells at 4° C. for 2 hr. Cells were then washed four times with PBS containing 1% BSA to remove unbound virus. The lysed cells were quantified for HIV p24 content by ELISA. Percentage of viral binding was expressed as relative percentage of the p24 reading from the cells without the antibodies (No MAb), which was set as 100%.

A post-attachment assay was performed using the QH-HA H5N1 pseudovirus. The virus was added to MDCK cells plated 18 hr before test, and incubated at 4° C. for 6 hr. After washing the cells three times with cold PBS to remove unbound virus, serially diluted MAbs HA-3 and HA-7, as well as control antibodies to SARS RBD and IgG-Fc, were added to the MDCK monolayer for 2 hr at 4° C. Fresh DMEM was added to the monolayer and cells were incubated at 37° C. Luciferase activity of the cells was then measured 72 hr post-infection. Percentage of viral entry was expressed as relative percentage of the luciferase reading from the cells without the antibodies (No Ab), which was set as 100% (% viral entry=luciferase reading of Abs/No Ab*100%).

Figure 18:
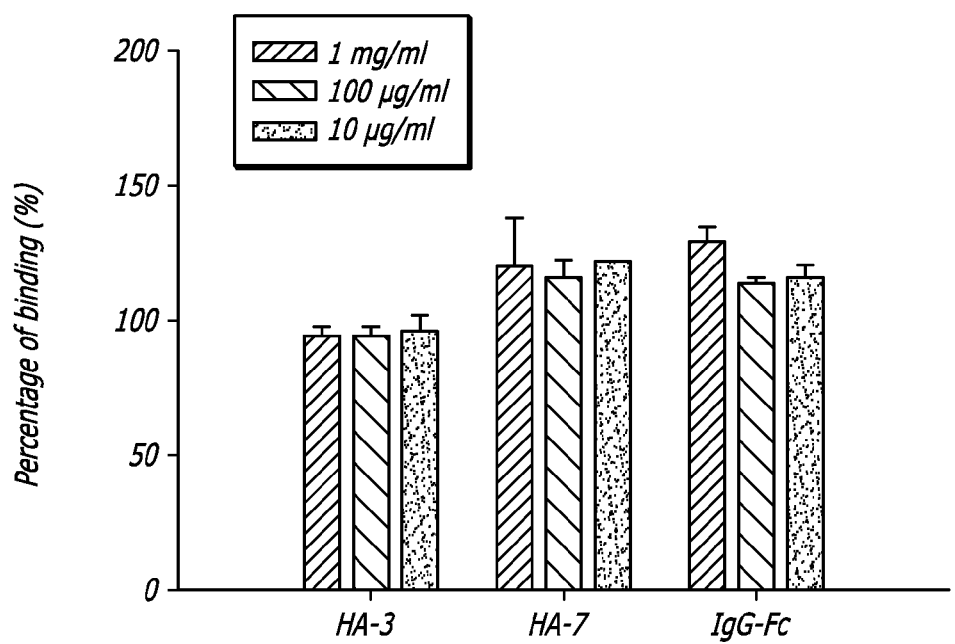
FIG. 18 depicts the binding of MAbs HA-3 and HA-7 to H5N1 pseudovirus, as measured by virus binding assay using QH-HA pseudovirus in virus-infected MDCK cells.

Results from the virus binding assay showed that increasing the concentration of the two neutralizing MAbs did not decrease the binding of the virus to MDCK cells, which were similar to those from the negative control human IgG Fc (FIG. 18). These results suggest that the inhibition of H5N1 viruses by MAbs HA-3 and HA-7 is not through the process of blocking the receptor binding.

Figures 19, 20:
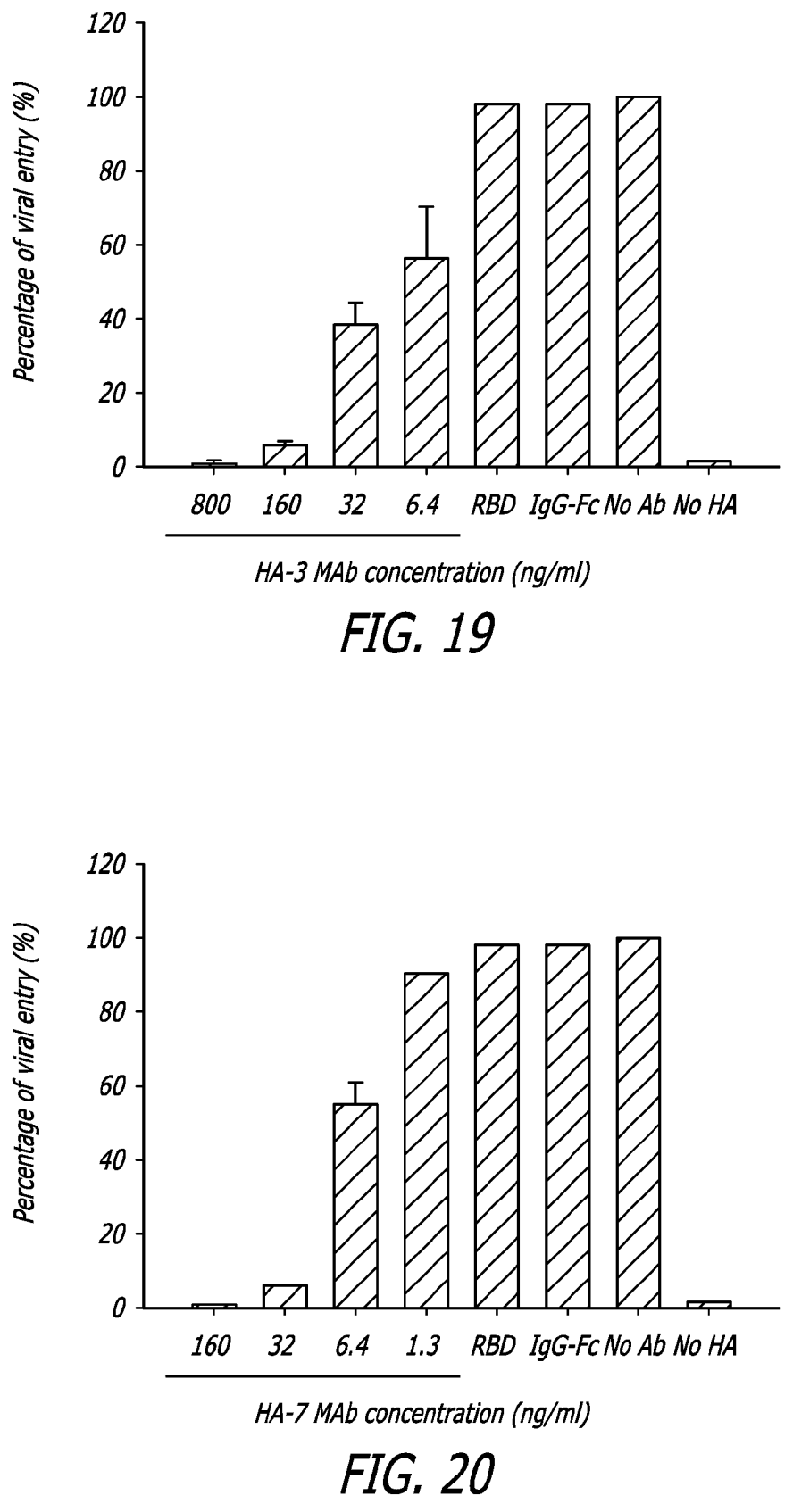

A post-attachment assay was further performed to characterize the mechanism of these two MAbs. Results depicted in FIGS. 19 and 20 indicates that both HA-3 and HA-7 inhibited the post-attachment processes in a dose-dependant manner, while the negative controls Abs (SARS RBD and human IgG-Fc) did not neutralize virus entry even at the highest concentration of 10 µg/ml, confirming that MAbs HA-3 and HA-7 inhibited virus entry at the post-attachment process rather than the receptor binding process.

Unless otherwise indicated, all numbers expressing quantities of ingredients, properties such as molecular weight, reaction conditions, and so forth used in the specification and claims are to be understood as being modified in all instances by the term "about". Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A neutralizing antibody specifically binding an epitope of the HA1 domain of influenza virus H5N1 hemagglutinin, the epitope comprising the amino acid sequence consisting of SEQ ID NO:15, and wherein the antibody competes for specific binding to SEQ ID NO:15 with a murine monoclonal antibody secreted by hybridoma HA-3 (ATCC accession number PTA-12174) or hybridoma HA-7 (ATCC accession number PTA-12173), wherein the neutralizing antibody is a humanized antibody or a chimeric antibody.

2. The neutralizing antibody of claim 1 or an antigen binding fragment thereof specifically binding the epitope comprising the amino acid sequence consisting of SEQ ID NO: 15.

3. A pharmaceutical formulation for neutralizing influenza virus comprising a neutralizing antibody according to claim 1.

4. The pharmaceutical formulation of claim 3, wherein the formulation further comprises at least one pharmaceutically acceptable excipient.

5. The pharmaceutical formulation of claim 3, wherein the formulation is for injection.

6. A method of treating influenza virus infection in a subject in need thereof comprising administering a therapeutically effective amount of the neutralizing antibody of claim 1 and thereby treating influenza virus infection in the subject.

* * * * *

SEQUENCE LISTING

```
<160> NUMBER OF SEQ ID NOS: 22

<210> SEQ ID NO 1
<211> LENGTH: 567
<212> TYPE: PRT
<213> ORGANISM: Influenza A virus

<400> SEQUENCE: 1

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Gln Gly Thr Pro Ser Phe Phe
145                 150                 155                 160

Arg Asn Val Val Trp Leu Ile Lys Lys Asn Asn Thr Tyr Pro Thr Ile
                165                 170                 175

Lys Arg Ser Tyr Asn Asn Thr Asn Gln Glu Asp Leu Leu Ile Leu Trp
            180                 185                 190

Gly Ile His His Ser Asn Asp Ala Ala Glu Gln Thr Lys Leu Tyr Gln
        195                 200                 205
```

```
Asn Pro Thr Thr Tyr Ile Ser Val Gly Thr Ser Thr Leu Asn Gln Arg
    210                 215                 220

Leu Val Pro Lys Ile Ala Thr Arg Ser Lys Val Asn Gly Gln Asn Gly
225                 230                 235                 240

Arg Met Asp Phe Phe Trp Thr Ile Leu Lys Pro Asn Asp Ala Ile Asn
                    245                 250                 255

Phe Glu Ser Asn Gly Asn Phe Ile Ala Pro Glu Tyr Ala Tyr Lys Ile
                260                 265                 270

Val Lys Lys Gly Asp Ser Ala Ile Val Lys Ser Glu Val Glu Tyr Gly
            275                 280                 285

Asn Cys Asn Thr Lys Cys Gln Thr Pro Ile Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
                325                 330                 335

Pro Leu Arg Glu Arg Arg Arg Lys Arg Gly Leu Phe Gly Ala Ile Ala
                340                 345                 350

Gly Phe Ile Glu Gly Gly Trp Gln Gly Met Val Asp Gly Trp Tyr Gly
                355                 360                 365

Tyr His His Ser Asn Glu Gln Gly Ser Gly Tyr Ala Ala Asp Lys Glu
            370                 375                 380

Ser Thr Gln Lys Ala Ile Asp Gly Val Thr Asn Lys Val Asn Ser Ile
385                 390                 395                 400

Ile Asp Lys Met Asn Thr Gln Phe Glu Ala Val Gly Arg Glu Phe Asn
                405                 410                 415

Asn Leu Glu Arg Arg Ile Glu Asn Leu Asn Lys Lys Met Glu Asp Gly
                420                 425                 430

Phe Leu Asp Val Trp Thr Tyr Asn Ala Glu Leu Leu Val Leu Met Glu
            435                 440                 445

Asn Glu Arg Thr Leu Asp Phe His Asp Ser Asn Val Lys Asn Leu Tyr
    450                 455                 460

Asp Lys Val Arg Leu Gln Leu Arg Asp Asn Ala Lys Glu Leu Gly Asn
465                 470                 475                 480

Gly Cys Phe Glu Phe Tyr His Lys Cys Asp Asn Glu Cys Met Glu Ser
                485                 490                 495

Val Arg Asn Gly Thr Tyr Asp Tyr Pro Gln Tyr Ser Glu Glu Ala Arg
                500                 505                 510

Leu Lys Arg Glu Glu Ile Ser Gly Val Lys Leu Glu Ser Ile Gly Thr
            515                 520                 525

Tyr Gln Ile Leu Ser Ile Tyr Ser Thr Val Ala Ser Ser Leu Ala Leu
            530                 535                 540

Ala Ile Met Val Ala Gly Leu Ser Leu Trp Met Cys Ser Asn Gly Ser
545                 550                 555                 560

Leu Gln Cys Arg Ile Cys Ile
                565

<210> SEQ ID NO 2
<211> LENGTH: 320
<212> TYPE: PRT
<213> ORGANISM: Influenza A virus

<400> SEQUENCE: 2

Ile Cys Ile Gly Tyr His Ala Asn Asn Ser Thr Glu Gln Val Asp Thr
1               5                   10                  15
```

```
Ile Met Glu Lys Asn Val Thr Val Thr His Ala Gln Asp Ile Leu Glu
            20                  25                  30

Lys Thr His Asn Gly Lys Leu Cys Asp Leu Asp Gly Val Lys Pro Leu
        35                  40                  45

Ile Leu Arg Asp Cys Ser Val Ala Gly Trp Leu Leu Gly Asn Pro Met
 50                  55                  60

Cys Asp Glu Phe Ile Asn Val Pro Glu Trp Ser Tyr Ile Val Glu Lys
 65                  70                  75                  80

Ala Asn Pro Ala Asn Asp Leu Cys Tyr Pro Gly Asn Phe Asn Asp Tyr
                85                  90                  95

Glu Glu Leu Lys His Leu Leu Ser Arg Ile Asn His Phe Glu Lys Ile
            100                 105                 110

Gln Ile Ile Pro Lys Ser Ser Trp Ser Asp His Glu Ala Ser Ser Gly
        115                 120                 125

Val Ser Ser Ala Cys Pro Tyr Gln Gly Thr Pro Ser Phe Phe Arg Asn
130                 135                 140

Val Val Trp Leu Ile Lys Lys Asn Asn Thr Tyr Pro Thr Ile Lys Arg
145                 150                 155                 160

Ser Tyr Asn Asn Thr Asn Gln Glu Asp Leu Leu Ile Leu Trp Gly Ile
                165                 170                 175

His His Ser Asn Asp Ala Ala Glu Gln Thr Lys Leu Tyr Gln Asn Pro
            180                 185                 190

Thr Thr Tyr Ile Ser Val Gly Thr Ser Thr Leu Asn Gln Arg Leu Val
        195                 200                 205

Pro Lys Ile Ala Thr Arg Ser Lys Val Asn Gly Gln Asn Gly Arg Met
210                 215                 220

Asp Phe Phe Trp Thr Ile Leu Lys Pro Asn Asp Ala Ile Asn Phe Glu
225                 230                 235                 240

Ser Asn Gly Asn Phe Ile Ala Pro Glu Tyr Ala Tyr Lys Ile Val Lys
                245                 250                 255

Lys Gly Asp Ser Ala Ile Val Lys Ser Glu Val Glu Tyr Gly Asn Cys
            260                 265                 270

Asn Thr Lys Cys Gln Thr Pro Ile Gly Ala Ile Asn Ser Ser Met Pro
        275                 280                 285

Phe His Asn Ile His Pro Leu Thr Ile Gly Glu Cys Pro Lys Tyr Val
290                 295                 300

Lys Ser Asn Lys Leu Val Leu Ala Thr Gly Leu Arg Asn Ser Pro Leu
305                 310                 315                 320

<210> SEQ ID NO 3
<211> LENGTH: 27
<212> TYPE: PRT
<213> ORGANISM: Artificial Sequence
<220> FEATURE:
<223> OTHER INFORMATION: Fodon linker sequence

<400> SEQUENCE: 3

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25

<210> SEQ ID NO 4
<211> LENGTH: 229
<212> TYPE: PRT
<213> ORGANISM: Homo sapiens
```

<400> SEQUENCE: 4

```
Arg Ser Asp Lys Thr His Thr Cys Pro Pro Cys Pro Ala Pro Glu Leu
1               5                   10                  15
Leu Gly Gly Pro Ser Val Phe Leu Phe Pro Pro Lys Pro Lys Asp Thr
            20                  25                  30
Leu Met Ile Ser Arg Thr Pro Glu Val Thr Cys Val Val Val Asp Val
        35                  40                  45
Ser His Glu Asp Pro Glu Val Lys Phe Asn Trp Tyr Val Asp Gly Val
    50                  55                  60
Glu Val His Asn Ala Lys Thr Lys Pro Arg Glu Glu Gln Tyr Asn Ser
65                  70                  75                  80
Thr Tyr Arg Val Val Ser Val Leu Thr Val Leu His Gln Asp Trp Leu
                85                  90                  95
Asn Gly Lys Glu Tyr Lys Cys Lys Val Ser Asn Lys Ala Leu Pro Ala
            100                 105                 110
Pro Ile Glu Lys Thr Ile Ser Lys Ala Lys Gly Gln Pro Arg Glu Pro
        115                 120                 125
Gln Val Tyr Thr Leu Pro Pro Ser Arg Glu Glu Met Thr Lys Asn Gln
    130                 135                 140
Val Ser Leu Thr Cys Leu Val Lys Gly Phe Tyr Pro Ser Asp Ile Ala
145                 150                 155                 160
Val Glu Trp Glu Ser Asn Gly Gln Pro Glu Asn Asn Tyr Lys Thr Thr
                165                 170                 175
Pro Pro Val Leu Asp Ser Asp Gly Ser Phe Phe Leu Tyr Ser Lys Leu
            180                 185                 190
Thr Val Asp Lys Ser Arg Trp Gln Gln Gly Asn Val Phe Ser Cys Ser
        195                 200                 205
Val Met His Glu Ala Leu His Asn His Tyr Thr Gln Lys Ser Leu Ser
    210                 215                 220
Leu Ser Pro Gly Lys
225
```

<210> SEQ ID NO 5
<211> LENGTH: 576
<212> TYPE: PRT
<213> ORGANISM: Artificial Sequence
<220> FEATURE:
<223> OTHER INFORMATION: A/Anhui/1/2005(H5N1) HA1(+3-322)-Fd-hFc fusion
      protein

<400> SEQUENCE: 5

```
Ile Cys Ile Gly Tyr His Ala Asn Asn Ser Thr Glu Gln Val Asp Thr
1               5

```
Gln Ile Ile Pro Lys Ser Ser Trp Ser Asp His Glu Ala Ser Ser Gly
        115                 120                 125

Val Ser Ser Ala Cys Pro Tyr Gln Gly Thr Pro Ser Phe Phe Arg Asn
130                 135                 140

Val Val Trp Leu Ile Lys Lys Asn Asn Thr Tyr Pro Thr Ile Lys Arg
145                 150                 155                 160

Ser Tyr Asn Asn Thr Asn Gln Glu Asp Leu Leu Ile Leu Trp Gly Ile
                165                 170                 175

His His Ser Asn Asp Ala Ala Glu Gln Thr Lys Leu Tyr Gln Asn Pro
            180                 185                 190

Thr Thr Tyr Ile Ser Val Gly Thr Ser Thr Leu Asn Gln Arg Leu Val
        195                 200                 205

Pro Lys Ile Ala Thr Arg Ser Lys Val Asn Gly Gln Asn Gly Arg Met
    210                 215                 220

Asp Phe Phe Trp Thr Ile Leu Lys Pro Asn Asp Ala Ile Asn Phe Glu
225                 230                 235                 240

Ser Asn Gly Asn Phe Ile Ala Pro Glu Tyr Ala Tyr Lys Ile Val Lys
                245                 250                 255

Lys Gly Asp Ser Ala Ile Val Lys Ser Glu Val Glu Tyr Gly Asn Cys
            260                 265                 270

Asn Thr Lys Cys Gln Thr Pro Ile Gly Ala Ile Asn Ser Ser Met Pro
        275                 280                 285

Phe His Asn Ile His Pro Leu Thr Ile Gly Glu Cys Pro Lys Tyr Val
    290                 295                 300

Lys Ser Asn Lys Leu Val Leu Ala Thr Gly Leu Arg Asn Ser Pro Leu
305                 310                 315                 320

Gly Tyr Ile Pro Glu Ala Pro Arg Asp Gly Gln Ala Tyr Val Arg Lys
                325                 330                 335

Asp Gly Glu Trp Val Leu Leu Ser Thr Phe Leu Arg Ser Asp Lys Thr
            340                 345                 350

His Thr Cys Pro Pro Cys Pro Ala Pro Glu Leu Leu Gly Gly Pro Ser
        355                 360                 365

Val Phe Leu Phe Pro Pro Lys Pro Lys Asp Thr Leu Met Ile Ser Arg
    370                 375                 380

Thr Pro Glu Val Thr Cys Val Val Val Asp Val Ser His Glu Asp Pro
385                 390                 395                 400

Glu Val Lys Phe Asn Trp Tyr Val Asp Gly Val Glu Val His Asn Ala
                405                 410                 415

Lys Thr Lys Pro Arg Glu Glu Gln Tyr Asn Ser Thr Tyr Arg Val Val
            420                 425                 430

Ser Val Leu Thr Val Leu His Gln Asp Trp Leu Asn Gly Lys Glu Tyr
        435                 440                 445

Lys Cys Lys Val Ser Asn Lys Ala Leu Pro Ala Pro Ile Glu Lys Thr
    450                 455                 460

Ile Ser Lys Ala Lys Gly Gln Pro Arg Glu Pro Gln Val Tyr Thr Leu
465                 470                 475                 480

Pro Pro Ser Arg Glu Glu Met Thr Lys Asn Gln Val Ser Leu Thr Cys
                485                 490                 495

Leu Val Lys Gly Phe Tyr Pro Ser Asp Ile Ala Val Glu Trp Glu Ser
            500                 505                 510

Asn Gly Gln Pro Glu Asn Asn Tyr Lys Thr Thr Pro Pro Val Leu Asp
        515                 520                 525
```

```
Ser Asp Gly Ser Phe Phe Leu Tyr Ser Lys Leu Thr Val Asp Lys Ser
            530                 535                 540

Arg Trp Gln Gln Gly Asn Val Phe Ser Cys Ser Val Met His Glu Ala
545                 550                 555                 560

Leu His Asn His Tyr Thr Gln Lys Ser Leu Ser Leu Ser Pro Gly Lys
                565                 570                 575

<210> SEQ ID NO 6
<211> LENGTH: 549
<212> TYPE: PRT
<213> ORGANISM: Artificial Sequence
<220> FEATURE:
<223> OTHER INFORMATION: A/Anhui/1/2005(H5N1) HA1(+3-322)-hFc fusion
      protein

<400> SEQUENCE: 6

Ile Cys Ile Gly Tyr His Ala Asn Asn Ser Thr Glu Gln Val Asp Thr
1               5                   10                  15

Ile Met Glu Lys Asn Val Thr Val Thr His Ala Gln Asp Ile Leu Glu
            20                  25                  30

Lys Thr His Asn Gly Lys Leu Cys Asp Leu Asp Gly Val Lys Pro Leu
        35                  40                  45

Ile Leu Arg Asp Cys Ser Val Ala Gly Trp Leu Leu Gly Asn Pro Met
    50                  55                  60

Cys Asp Glu Phe Ile Asn Val Pro Glu Trp Ser Tyr Ile Val Glu Lys
65                  70                  75                  80

Ala Asn Pro Ala Asn Asp Leu Cys Tyr Pro Gly Asn Phe Asn Asp Tyr
                85                  90                  95

Glu Glu Leu Lys His Leu Leu Ser Arg Ile Asn His Phe Glu Lys Ile
            100                 105                 110

Gln Ile Ile Pro Lys Ser Ser Trp Ser Asp His Glu Ala Ser Ser Gly
        115                 120                 125

Val Ser Ser Ala Cys Pro Tyr Gln Gly Thr Pro Ser Phe Phe Arg Asn
130                 135                 140

Val Val Trp Leu Ile Lys Lys Asn Asn Thr Tyr Pro Thr Ile Lys Arg
145                 150                 155                 160

Ser Tyr Asn Asn Thr Asn Gln Glu Asp Leu Leu Ile Leu Trp Gly Ile
                165                 170                 175

His His Ser Asn Asp Ala Ala Glu Gln Thr Lys Leu Tyr Gln Asn Pro
            180                 185                 190

Thr Thr Tyr Ile Ser Val Gly Thr Ser Thr Leu Asn Gln Arg Leu Val
        195                 200                 205

Pro Lys Ile Ala Thr Arg Ser Lys Val Asn Gly Gln Asn Gly Arg Met
210                 215                 220

Asp Phe Phe Trp Thr Ile Leu Lys Pro Asn Asp Ala Ile Asn Phe Glu
225                 230                 235                 240

Ser Asn Gly Asn Phe Ile Ala Pro Glu Tyr Ala Tyr Lys Ile Val Lys
                245                 250                 255

Lys Gly Asp Ser Ala Ile Val Lys Ser Glu Val Glu Tyr Gly Asn Cys
            260                 265                 270

Asn Thr Lys Cys Gln Thr Pro Ile Gly Ala Ile Asn Ser Ser Met Pro
        275                 280                 285

Phe His Asn Ile His Pro Leu Thr Ile Gly Glu Cys Pro Lys Tyr Val
290                 295                 300

Lys Ser Asn Lys Leu Val Leu Ala Thr Gly Leu Arg Asn Ser Pro Leu
305                 310                 315                 320
```

```
Arg Ser Asp Lys Thr His Thr Cys Pro Pro Cys Pro Ala Pro Glu Leu
            325                 330                 335

Leu Gly Gly Pro Ser Val Phe Leu Phe Pro Pro Lys Pro Lys Asp Thr
        340                 345                 350

Leu Met Ile Ser Arg Thr Pro Glu Val Thr Cys Val Val Val Asp Val
            355                 360                 365

Ser His Glu Asp Pro Glu Val Lys Phe Asn Trp Tyr Val Asp Gly Val
370                 375                 380

Glu Val His Asn Ala Lys Thr Lys Pro Arg Glu Glu Gln Tyr Asn Ser
385                 390                 395                 400

Thr Tyr Arg Val Val Ser Val Leu Thr Val Leu His Gln Asp Trp Leu
            405                 410                 415

Asn Gly Lys Glu Tyr Lys Cys Lys Val Ser Asn Lys Ala Leu Pro Ala
            420                 425                 430

Pro Ile Glu Lys Thr Ile Ser Lys Ala Lys Gly Gln Pro Arg Glu Pro
            435                 440                 445

Gln Val Tyr Thr Leu Pro Pro Ser Arg Glu Glu Met Thr Lys Asn Gln
        450                 455                 460

Val Ser Leu Thr Cys Leu Val Lys Gly Phe Tyr Pro Ser Asp Ile Ala
465                 470                 475                 480

Val Glu Trp Glu Ser Asn Gly Gln Pro Glu Asn Asn Tyr Lys Thr Thr
            485                 490                 495

Pro Pro Val Leu Asp Ser Asp Gly Ser Phe Phe Leu Tyr Ser Lys Leu
            500                 505                 510

Thr Val Asp Lys Ser Arg Trp Gln Gln Gly Asn Val Phe Ser Cys Ser
            515                 520                 525

Val Met His Glu Ala Leu His Asn His Tyr Thr Gln Lys Ser Leu Ser
530                 535                 540

Leu Ser Pro Gly Lys
545

<210> SEQ ID NO 7
<211> LENGTH: 347
<212> TYPE: PRT
<213> ORGANISM: Artificial Sequence
<220> FEATURE:
<223> OTHER INFORMATION: A/Anhui/1/2005(H5N1) HA1(+3-322)-Fd fusion
      protein

<400> SEQUENCE: 7

Ile Cys Ile Gly Tyr His Ala Asn Asn Ser Thr Glu Gln Val Asp Thr
1               5                   10                  15

Ile Met Glu Lys Asn Val Thr Val Thr His Ala Gln Asp Ile Leu Glu
            20                  25                  30

Lys Thr His Asn Gly Lys Leu Cys Asp Leu Asp Gly Val Lys Pro Leu
        35                  40                  45

Ile Leu Arg Asp Cys Ser Val Ala Gly Trp Leu Leu Gly Asn Pro Met
    50                  55                  60

Cys Asp Glu Phe Ile Asn Val Pro Glu Trp Ser Tyr Ile Val Glu Lys
65                  70                  75                  80

Ala Asn Pro Ala Asn Asp Leu Cys Tyr Pro Gly Asn Phe Asn Asp Tyr
                85                  90                  95

Glu Glu Leu Lys His Leu Leu Ser Arg Ile Asn His Phe Glu Lys Ile
            100                 105                 110

Gln Ile Ile Pro Lys Ser Ser Trp Ser Asp His Glu Ala Ser Ser Gly
```

```
            115                 120                 125
Val Ser Ser Ala Cys Pro Tyr Gln Gly Thr Pro Ser Phe Phe Arg Asn
130                 135                 140

Val Val Trp Leu Ile Lys Lys Asn Asn Thr Tyr Pro Thr Ile Lys Arg
145                 150                 155                 160

Ser Tyr Asn Asn Thr Asn Gln Glu Asp Leu Leu Ile Leu Trp Gly Ile
                165                 170                 175

His His Ser Asn Asp Ala Ala Glu Gln Thr Lys Leu Tyr Gln Asn Pro
                180                 185                 190

Thr Thr Tyr Ile Ser Val Gly Thr Ser Thr Leu Asn Gln Arg Leu Val
                195                 200                 205

Pro Lys Ile Ala Thr Arg Ser Lys Val Asn Gly Gln Asn Gly Arg Met
210                 215                 220

Asp Phe Phe Trp Thr Ile Leu Lys Pro Asn Asp Ala Ile Asn Phe Glu
225                 230                 235                 240

Ser Asn Gly Asn Phe Ile Ala Pro Glu Tyr Ala Tyr Lys Ile Val Lys
                245                 250                 255

Lys Gly Asp Ser Ala Ile Val Lys Ser Glu Val Glu Tyr Gly Asn Cys
                260                 265                 270

Asn Thr Lys Cys Gln Thr Pro Ile Gly Ala Ile Asn Ser Ser Met Pro
                275                 280                 285

Phe His Asn Ile His Pro Leu Thr Ile Gly Glu Cys Pro Lys Tyr Val
                290                 295                 300

Lys Ser Asn Lys Leu Val Leu Ala Thr Gly Leu Arg Asn Ser Pro Leu
305                 310                 315                 320

Gly Tyr Ile Pro Glu Ala Pro Arg Asp Gly Gln Ala Tyr Val Arg Lys
                325                 330                 335

Asp Gly Glu Trp Val Leu Leu Ser Thr Phe Leu
                340                 345

<210> SEQ ID NO 8
<211> LENGTH: 326
<212> TYPE: PRT
<213> ORGANISM: Artificial Sequence
<220> FEATURE:
<223> OTHER INFORMATION: A/Anhui/1/2005(H5N1) HA1(+3-322)-His fusion
      protein

<400> SEQUENCE: 8

Ile Cys Ile Gly Tyr His Ala Asn Asn Ser Thr Glu Gln Val Asp Thr
1               5                   10                  15

Ile Met Glu Lys Asn Val Thr Val Thr His Ala Gln Asp Ile Leu Glu
                20                  25                  30

Lys Thr His Asn Gly Lys Leu Cys Asp Leu Asp Gly Val Lys Pro Leu
            35                  40                  45

Ile Leu Arg Asp Cys Ser Val Ala Gly Trp Leu Leu Gly Asn Pro Met
        50                  55                  60

Cys Asp Glu Phe Ile Asn Val Pro Glu Trp Ser Tyr Ile Val Glu Lys
65                  70                  75                  80

Ala Asn Pro Ala Asn Asp Leu Cys Tyr Pro Gly Asn Phe Asn Asp Tyr
                85                  90                  95

Glu Glu Leu Lys His Leu Leu Ser Arg Ile Asn His Phe Glu Lys Ile
                100                 105                 110

Gln Ile Ile Pro Lys Ser Ser Trp Ser Asp His Glu Ala Ser Ser Gly
            115                 120                 125
```

```
Val Ser Ser Ala Cys Pro Tyr Gln Gly Thr Pro Ser Phe Phe Arg Asn
130                 135                 140

Val Val Trp Leu Ile Lys Lys Asn Asn Thr Tyr Pro Thr Ile Lys Arg
145                 150                 155                 160

Ser Tyr Asn Asn Thr Asn Gln Glu Asp Leu Leu Ile Leu Trp Gly Ile
                165                 170                 175

His His Ser Asn Asp Ala Ala Glu Gln Thr Lys Leu Tyr Gln Asn Pro
            180                 185                 190

Thr Thr Tyr Ile Ser Val Gly Thr Ser Thr Leu Asn Gln Arg Leu Val
        195                 200                 205

Pro Lys Ile Ala Thr Arg Ser Lys Val Asn Gly Gln Asn Gly Arg Met
210                 215                 220

Asp Phe Phe Trp Thr Ile Leu Lys Pro Asn Asp Ala Ile Asn Phe Glu
225                 230                 235                 240

Ser Asn Gly Asn Phe Ile Ala Pro Glu Tyr Ala Tyr Lys Ile Val Lys
                245                 250                 255

Lys Gly Asp Ser Ala Ile Val Lys Ser Glu Val Glu Tyr Gly Asn Cys
            260                 265                 270

Asn Thr Lys Cys Gln Thr Pro Ile Gly Ala Ile Asn Ser Ser Met Pro
        275                 280                 285

Phe His Asn Ile His Pro Leu Thr Ile Gly Glu Cys Pro Lys Tyr Val
    290                 295                 300

Lys Ser Asn Lys Leu Val Leu Ala Thr Gly Leu Arg Asn Ser Pro Leu
305                 310                 315                 320

His His His His His His
                325

<210> SEQ ID NO 9
<211> LENGTH: 218
<212> TYPE: PRT
<213> ORGANISM: Influenza A virus

<400> SEQUENCE: 9

Leu Ser Arg Ile Asn His Phe Glu Lys Ile Gln Ile Ile Pro Lys Ser
1               5                   10                  15

Ser Trp Ser Asp His Glu Ala Ser Ser Gly Val Ser Ser Ala Cys Pro
                20                  25                  30

Tyr Gln Gly Thr Pro Ser Phe Phe Arg Asn Val Val Trp Leu Ile Lys
            35                  40                  45

Lys Asn Asn Thr Tyr Pro Thr Ile Lys Arg Ser Tyr Asn Asn Thr Asn
50                  55                  60

Gln Glu Asp Leu Leu Ile Leu Trp Gly Ile His His Ser Asn Asp Ala
65                  70                  75                  80

Ala Glu Gln Thr Lys Leu Tyr Gln Asn Pro Thr Thr Tyr Ile Ser Val
                85                  90                  95

Gly Thr Ser Thr Leu Asn Gln Arg Leu Val Pro Lys Ile Ala Thr Arg
            100                 105                 110

Ser Lys Val Asn Gly Gln Asn Gly Arg Met Asp Phe Phe Trp Thr Ile
        115                 120                 125

Leu Lys Pro Asn Asp Ala Ile Asn Phe Glu Ser Asn Gly Asn Phe Ile
130                 135                 140

Ala Pro Glu Tyr Ala Tyr Lys Ile Val Lys Lys Gly Asp Ser Ala Ile
145                 150                 155                 160

Val Lys Ser Glu Val Glu Tyr Gly Asn Cys Asn Thr Lys Cys Gln Thr
                165                 170                 175
```

```
Pro Ile Gly Ala Ile Asn Ser Ser Met Pro Phe His Asn Ile His Pro
            180                 185                 190

Leu Thr Ile Gly Glu Cys Pro Lys Tyr Val Lys Ser Asn Lys Leu Val
        195                 200                 205

Leu Ala Thr Gly Leu Arg Asn Ser Pro Leu
        210                 215

<210> SEQ ID NO 10
<211> LENGTH: 155
<212> TYPE: PRT
<213> ORGANISM: Influenza A virus

<400> SEQUENCE: 10

Leu Ser Arg Ile Asn His Phe Glu Lys Ile Gln Ile Ile Pro Lys Ser
1               5                   10                  15

Ser Trp Ser Asp His Glu Ala Ser Ser Gly Val Ser Ser Ala Cys Pro
            20                  25                  30

Tyr Gln Gly Thr Pro Ser Phe Phe Arg Asn Val Val Trp Leu Ile Lys
        35                  40                  45

Lys Asn Asn Thr Tyr Pro Thr Ile Lys Arg Ser Tyr Asn Asn Thr Asn
    50                  55                  60

Gln Glu Asp Leu Leu Ile Leu Trp Gly Ile His His Ser Asn Asp Ala
65                  70                  75                  80

Ala Glu Gln Thr Lys Leu Tyr Gln Asn Pro Thr Thr Tyr Ile Ser Val
                85                  90                  95

Gly Thr Ser Thr Leu Asn Gln Arg Leu Val Pro Lys Ile Ala Thr Arg
            100                 105                 110

Ser Lys Val Asn Gly Gln Asn Gly Arg Met Asp Phe Phe Trp Thr Ile
        115                 120                 125

Leu Lys Pro Asn Asp Ala Ile Asn Phe Glu Ser Asn Gly Asn Phe Ile
    130                 135                 140

Ala Pro Glu Tyr Ala Tyr Lys Ile Val Lys Lys
145                 150                 155

<210> SEQ ID NO 11
<211> LENGTH: 257
<212> TYPE: PRT
<213> ORGANISM: Influenza A virus

<400> SEQUENCE: 11

Ile Cys Ile Gly Tyr His Ala Asn Asn Ser Thr Glu Gln Val Asp Thr
1               5                   10                  15

Ile Met Glu L

```
Val Ser Ser Ala Cys Pro Tyr Gln Gly Thr Pro Ser Phe Phe Arg Asn
    130                 135                 140

Val Val Trp Leu Ile Lys Lys Asn Asn Thr Tyr Pro Thr Ile Lys Arg
145                 150                 155                 160

Ser Tyr Asn Asn Thr Asn Gln Glu Asp Leu Leu Ile Leu Trp Gly Ile
                165                 170                 175

His His Ser Asn Asp Ala Ala Glu Gln Thr Lys Leu Tyr Gln Asn Pro
            180                 185                 190

Thr Thr Tyr Ile Ser Val Gly Thr Ser Thr Leu Asn Gln Arg Leu Val
        195                 200                 205

Pro Lys Ile Ala Thr Arg Ser Lys Val Asn Gly Gln Asn Gly Arg Met
    210                 215                 220

Asp Phe Phe Trp Thr Ile Leu Lys Pro Asn Asp Ala Ile Asn Phe Glu
225                 230                 235                 240

Ser Asn Gly Asn Phe Ile Ala Pro Glu Tyr Ala Tyr Lys Ile Val Lys
                245                 250                 255

Lys

<210> SEQ ID NO 12
<211> LENGTH: 232
<212> TYPE: PRT
<213> ORGANISM: Influenza A virus

<400> SEQUENCE: 12

His Ala Gln Asp Ile Leu Glu Lys Thr His Asn Gly Lys Leu Cys Asp
1               5                   10                  15

Leu Asp Gly Val Lys Pro Leu Ile Leu Arg Asp Cys Ser Val Ala Gly
            20                  25                  30

Trp Leu Leu Gly Asn Pro Met Cys Asp Glu Phe Ile Asn Val Pro Glu
        35                  40                  45

Trp Ser Tyr Ile Val Glu Lys Ala Asn Pro Ala Asn Asp Leu Cys Tyr
    50                  55                  60

Pro Gly Asn Phe Asn Asp Tyr Glu Glu Leu Lys His Leu Leu Ser Arg
65                  70                  75                  80

Ile Asn His Phe Glu Lys Ile Gln Ile Ile Pro Lys Ser Ser Trp Ser
                85                  90                  95

Asp His Glu Ala Ser Ser Gly Val Ser Ser Ala Cys Pro Tyr Gln Gly
            100                 105                 110

Thr Pro Ser Phe Phe Arg Asn Val Val Trp Leu Ile Lys Lys Asn Asn
        115                 120                 125

Thr Tyr Pro Thr Ile Lys Arg Ser Tyr Asn Asn Thr Asn Gln Glu Asp
    130                 135                 140

Leu Leu Ile Leu Trp Gly Ile His His Ser Asn Asp Ala Ala Glu Gln
145                 150                 155                 160

Thr Lys Leu Tyr Gln Asn Pro Thr Thr Tyr Ile Ser Val Gly Thr Ser
                165                 170                 175

Thr Leu Asn Gln Arg Leu Val Pro Lys Ile Ala Thr Arg Ser Lys Val
            180                 185                 190

Asn Gly Gln Asn Gly Arg Met Asp Phe Phe Trp Thr Ile Leu Lys Pro
        195                 200                 205

Asn Asp Ala Ile Asn Phe Glu Ser Asn Gly Asn Phe Ile Ala Pro Glu
    210                 215                 220

Tyr Ala Tyr Lys Ile Val Lys Lys
225                 230
```

```
<210> SEQ ID NO 13
<211> LENGTH: 215
<212> TYPE: PRT
<213> ORGANISM: Influenza A virus

<400> SEQUENCE: 13

Asp Gly Val Lys Pro Leu Ile Leu Arg Asp Cys Ser Val Ala Gly Trp
1               5                   10                  15

Leu Leu Gly Asn Pro Met Cys Asp Glu Phe Ile Asn Val Pro Glu Trp
            20                  25                  30

Ser Tyr Ile Val Glu Lys Ala Asn Pro Ala Asn Asp Leu Cys Tyr Pro
        35                  40                  45

Gly Asn Phe Asn Asp Tyr Glu Glu Leu Lys His Leu Leu Ser Arg Ile
    50                  55                  60

Asn His Phe Glu Lys Ile Gln Ile Ile Pro Lys Ser Ser Trp Ser Asp
65                  70                  75                  80

His Glu Ala Ser Ser Gly Val Ser Ser Ala Cys Pro Tyr Gln Gly Thr
                85                  90                  95

Pro Ser Phe Phe Arg Asn Val Val Trp Leu Ile Lys Lys Asn Asn Thr
            100                 105                 110

Tyr Pro Thr Ile Lys Arg Ser Tyr Asn Asn Thr Asn Gln Glu Asp Leu
        115                 120                 125

Leu Ile Leu Trp Gly Ile His His Ser Asn Asp Ala Ala Glu Gln Thr
    130                 135                 140

Lys Leu Tyr Gln Asn Pro Thr Thr Tyr Ile Ser Val Gly Thr Ser Thr
145                 150                 155                 160

Leu Asn Gln Arg Leu Val Pro Lys Ile Ala Thr Arg Ser Lys Val Asn
                165                 170                 175

Gly Gln Asn Gly Arg Met Asp Phe Phe Trp Thr Ile Leu Lys Pro Asn
            180                 185                 190

Asp Ala Ile Asn Phe Glu Ser Asn Gly Asn Phe Ile Ala Pro Glu Tyr
        195                 200                 205

Ala Tyr Lys Ile Val Lys Lys
        210                 215

<210> SEQ ID NO 14
<211> LENGTH: 188
<212> TYPE: PRT
<213> ORGANISM: Influenza A virus

<400> SEQUENCE: 14

Asn Val Pro Glu Trp Ser Tyr Ile Val Glu Lys Ala Asn Pro Ala Asn
1               5                   10                  15

Asp Leu Cys Tyr Pro Gly Asn Phe Asn Asp Tyr Glu Glu Leu Lys His
            20                  25                  30

Leu Leu Ser Arg Ile Asn His Phe Glu Lys Ile Gln Ile Ile Pro Lys
        35                  40                  45

Ser Ser Trp Ser Asp His Glu Ala Ser Ser Gly Val Ser Ser Ala Cys
    50                  55                  60

Pro Tyr Gln Gly Thr Pro Ser Phe Phe Arg Asn Val Val Trp Leu Ile
65                  70                  75                  80

Lys Lys Asn Asn Thr Tyr Pro Thr Ile Lys Arg Ser Tyr Asn Asn Thr
                85                  90                  95

Asn Gln Glu Asp Leu Leu Ile Leu Trp Gly Ile His His Ser Asn Asp
            100                 105                 110
```

```
Ala Ala Glu Gln Thr Lys Leu Tyr Gln Asn Pro Thr Thr Tyr Ile Ser
        115                 120                 125

Val Gly Thr Ser Thr Leu Asn Gln Arg Leu Val Pro Lys Ile Ala Thr
    130                 135                 140

Arg Ser Lys Val Asn Gly Gln Asn Gly Arg Met Asp Phe Phe Trp Thr
145                 150                 155                 160

Ile Leu Lys Pro Asn Asp Ala Ile Asn Phe Glu Ser Asn Gly Asn Phe
            165                 170                 175

Ile Ala Pro Glu Tyr Ala Tyr Lys Ile Val Lys Lys
            180                 185

<210> SEQ ID NO 15
<211> LENGTH: 44
<212> TYPE: PRT
<213> ORGANISM: Influenza A virus

<400> SEQUENCE: 15

Asn Val Pro Glu Trp Ser Tyr Ile Val Glu Lys Ala Asn Pro Ala Asn
1               5                   10                  15

Asp Leu Cys Tyr Pro Gly Asn Phe Asn Asp Tyr Glu Glu Leu Lys His
            20                  25                  30

Leu Leu Ser Arg Ile Asn His Phe Glu Lys Ile Gln
        35                  40

<210> SEQ ID NO 16
<211> LENGTH: 474
<212> TYPE: PRT
<213> ORGANISM: Artificial Sequence
<220> FEATURE:
<223> OTHER INFORMATION: A/Anhui/1/2005(H5N1) HA1(+105-322)-Fd-hFc
      fusion protein

<400> SEQUENCE: 16

Leu Ser Arg Ile Asn His Phe Glu Lys Ile Gln Ile Ile Pro Lys Ser
1               5                   10                  15

Ser Trp Ser Asp His Glu Ala Ser Ser Gly Val Ser Ser Ala Cys Pro
            20                  25                  30

Tyr Gln Gly Thr Pro Ser Phe Phe Arg Asn Val Val Trp Leu Ile Lys
        35                  40                  45

Lys Asn Asn Thr Tyr Pro Thr Ile Lys Arg Ser Tyr Asn Asn Thr Asn
    50                  55                  60

Gln Glu Asp Leu Leu Ile Leu Trp Gly Ile His His Ser Asn Asp Ala
65                  70                  75                  80

Ala Glu Gln Thr Lys Leu Tyr Gln Asn Pro Thr Thr Tyr Ile Ser Val
                85                  90                  95

Gly Thr Ser Thr Leu Asn Gln Arg Leu Val Pro Lys Ile Ala Thr Arg
            100                 105                 110

Ser Lys Val Asn Gly Gln Asn Gly Arg Met Asp Phe Phe Trp Thr Ile
        115                 120                 125

Leu Lys Pro Asn Asp Ala Ile Asn Phe Glu Ser Asn Gly Asn Phe Ile
    130                 135                 140

Ala Pro Glu Tyr Ala Tyr Lys Ile Val Lys Lys Gly Asp Ser Ala Ile
145                 150                 155                 160

Val Lys Ser Glu Val Glu Tyr Gly Asn Cys Asn Thr Lys Cys Gln Thr
                165                 170                 175

Pro Ile Gly Ala Ile Asn Ser Ser Met Pro Phe His Asn Ile His Pro
            180                 185                 190
```

```
Leu Thr Ile Gly Glu Cys Pro Lys Tyr Val Lys Ser Asn Lys Leu Val
            195                 200                 205

Leu Ala Thr Gly Leu Arg Asn Ser Pro Leu Gly Tyr Ile Pro Glu Ala
        210                 215                 220

Pro Arg Asp Gly Gln Ala Tyr Val Arg Lys Asp Gly Glu Trp Val Leu
225                 230                 235                 240

Leu Ser Thr Phe Leu Arg Ser Asp Lys Thr His Thr Cys Pro Pro Cys
            245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
            275                 280                 285

Val Val Val Asp Val Ser His Glu Asp Pro Glu Val Lys Phe Asn Trp
        290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
            325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
            355                 360                 365

Gln Pro Arg Glu Pro Gln Val Tyr Thr Leu Pro Pro Ser Arg Glu Glu
            370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
            405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
            435                 440                 445

Val Phe Ser Cys Ser Val Met His Glu Ala Leu His Asn His Tyr Thr
        450                 455                 460

Gln Lys Ser Leu Ser Leu Ser Pro Gly Lys
465                 470

<210> SEQ ID NO 17
<211> LENGTH: 411
<212> TYPE: PRT
<213> ORGANISM: Artificial Sequence
<220> FEATURE:
<223> OTHER INFORMATION: A/Anhui/1/2005(H5N1) HA1(+105-259)-Fd-hFc
      fusion protein

<400> SEQUENCE: 17

Leu Ser Arg Ile Asn His Phe Glu Lys Ile Gln Ile Ile Pro Lys Ser
1               5                   10                  15

Ser Trp Ser Asp His Glu Ala Ser Ser Gly Val Ser Ser Ala Cys Pro
            20                  25                  30

Tyr Gln Gly Thr Pro Ser Phe Phe Arg Asn Val Val Trp Leu Ile Lys
        35                  40                  45

Lys Asn Asn Thr Tyr Pro Thr Ile Lys Arg Ser Tyr Asn Asn Thr Asn
    50                  55                  60

Gln Glu Asp Leu Leu Ile Leu Trp Gly Ile His His Ser Asn Asp Ala
```

```
                65                  70                  75                  80
        Ala Glu Gln Thr Lys Leu Tyr Gln Asn Pro Thr Thr Tyr Ile Ser Val
                        85                  90                  95

Gly Thr Ser Thr Leu Asn Gln Arg Leu Val Pro Lys Ile Ala Thr Arg
                        100                 105                 110

Ser Lys Val Asn Gly Gln Asn Gly Arg Met Asp Phe Phe Trp Thr Ile
                        115                 120                 125

Leu Lys Pro Asn Asp Ala Ile Asn Phe Glu Ser Asn Gly Asn Phe Ile
                    130                 135                 140

Ala Pro Glu Tyr Ala Tyr Lys Ile Val Lys Gly Tyr Ile Pro Glu
        145                 150                 155                 160

Ala Pro Arg Asp Gly Gln Ala Tyr Val Arg Lys Asp Gly Glu Trp Val
                        165                 170                 175

Leu Leu Ser Thr Phe Leu Arg Ser Asp Lys Thr His Thr Cys Pro Pro
                        180                 185                 190

Cys Pro Ala Pro Glu Leu Leu Gly Gly Pro Ser Val Phe Leu Phe Pro
                        195                 200                 205

Pro Lys Pro Lys Asp Thr Leu Met Ile Ser Arg Thr Pro Glu Val Thr
                    210                 215                 220

Cys Val Val Val Asp Val Ser His Glu Asp Pro Glu Val Lys Phe Asn
        225                 230                 235                 240

Trp Tyr Val Asp Gly Val Glu Val His Asn Ala Lys Thr Lys Pro Arg
                        245                 250                 255

Glu Glu Gln Tyr Asn Ser Thr Tyr Arg Val Val Ser Val Leu Thr Val
                        260                 265                 270

Leu His Gln Asp Trp Leu Asn Gly Lys Glu Tyr Lys Cys Lys Val Ser
                    275                 280                 285

Asn Lys Ala Leu Pro Ala Pro Ile Glu Lys Thr Ile Ser Lys Ala Lys
                    290                 295                 300

Gly Gln Pro Arg Glu Pro Gln Val Tyr Thr Leu Pro Pro Ser Arg Glu
        305                 310                 315                 320

Glu Met Thr Lys Asn Gln Val Ser Leu Thr Cys Leu Val Lys Gly Phe
                        325                 330                 335

Tyr Pro Ser Asp Ile Ala Val Glu Trp Glu Ser Asn Gly Gln Pro Glu
                        340                 345                 350

Asn Asn Tyr Lys Thr Thr Pro Pro Val Leu Asp Ser Asp Gly Ser Phe
                    355                 360                 365

Phe Leu Tyr Ser Lys Leu Thr Val Asp Lys Ser Arg Trp Gln Gln Gly
            370                 375                 380

Asn Val Phe Ser Cys Ser Val Met His Glu Ala Leu His Asn His Tyr
        385                 390                 395                 400

Thr Gln Lys Ser Leu Ser Leu Ser Pro Gly Lys
                        405                 410

<210> SEQ ID NO 18
<211> LENGTH: 513
<212> TYPE: PRT
<213> ORGANISM: Artificial Sequence
<220> FEATURE:
<223> OTHER INFORMATION: A/Anhui/1/2005(H5N1) HA1(+3-259)-Fd-hFc fusion
      protein

<400> SEQUENCE: 18

Ile Cys Ile Gly Tyr His Ala Asn Asn Ser Thr Glu Gln Val Asp Thr
        1               5                   10                  15
```

-continued

```
Ile Met Glu Lys Asn Val Thr Val Thr His Ala Gln Asp Ile Leu Glu
             20                  25                  30
Lys Thr His Asn Gly Lys Leu Cys Asp Leu Asp Gly Val Lys Pro Leu
         35                  40                  45
Ile Leu Arg Asp Cys Ser Val Ala Gly Trp Leu Leu Gly Asn Pro Met
     50                  55                  60
Cys Asp Glu Phe Ile Asn Val Pro Glu Trp Ser Tyr Ile Val Glu Lys
 65                  70                  75                  80
Ala Asn Pro Ala Asn Asp Leu Cys Tyr Pro Gly Asn Phe Asn Asp Tyr
                 85                  90                  95
Glu Glu Leu Lys His Leu Leu Ser Arg Ile Asn His Phe Glu Lys Ile
            100                 105                 110
Gln Ile Ile Pro Lys Ser Ser Trp Ser Asp His Glu Ala Ser Ser Gly
        115                 120                 125
Val Ser Ser Ala Cys Pro Tyr Gln Gly Thr Pro Ser Phe Phe Arg Asn
    130                 135                 140
Val Val Trp Leu Ile Lys Lys Asn Asn Thr Tyr Pro Thr Ile Lys Arg
145                 150                 155                 160
Ser Tyr Asn Asn Thr Asn Gln Glu Asp Leu Leu Ile Leu Trp Gly Ile
                165                 170                 175
His His Ser Asn Asp Ala Ala Glu Gln Thr Lys Leu Tyr Gln Asn Pro
            180                 185                 190
Thr Thr Tyr Ile Ser Val Gly Thr Ser Thr Leu Asn Gln Arg Leu Val
        195                 200                 205
Pro Lys Ile Ala Thr Arg Ser Lys Val Asn Gly Gln Asn Gly Arg Met
    210                 215                 220
Asp Phe Phe Trp Thr Ile Leu Lys Pro Asn Asp Ala Ile Asn Phe Glu
225                 230                 235                 240
Ser Asn Gly Asn Phe Ile Ala Pro Glu Tyr Ala Tyr Lys Ile Val Lys
                245                 250                 255
Lys Gly Tyr Ile Pro Glu Ala Pro Arg Asp Gly Gln Ala Tyr Val Arg
            260                 265                 270
Lys Asp Gly Glu Trp Val Leu Leu Ser Thr Phe Leu Arg Ser Asp Lys
        275                 280                 285
Thr His Thr Cys Pro Pro Cys Pro Ala Pro Glu Leu Leu Gly Gly Pro
    290                 295                 300
Ser Val Phe Leu Phe Pro Pro Lys Pro Lys Asp Thr Leu Met Ile Ser
305                 310                 315                 320
Arg Thr Pro Glu Val Thr Cys Val Val Val Asp Val Ser His Glu Asp
                325                 330                 335
Pro Glu Val Lys Phe Asn Trp Tyr Val Asp Gly Val Glu Val His Asn
            340                 345                 350
Ala Lys Thr Lys Pro Arg Glu Glu Gln Tyr Asn Ser Thr Tyr Arg Val
        355                 360                 365
Val Ser Val Leu Thr Val Leu His Gln Asp Trp Leu Asn Gly Lys Glu
    370                 375                 380
Tyr Lys Cys Lys Val Ser Asn Lys Ala Leu Pro Ala Pro Ile Glu Lys
385                 390                 395                 400
Thr Ile Ser Lys Ala Lys Gly Gln Pro Arg Glu Pro Gln Val Tyr Thr
                405                 410                 415
Leu Pro Pro Ser Arg Glu Glu Met Thr Lys Asn Gln Val Ser Leu Thr
            420                 425                 430
Cys Leu Val Lys Gly Phe Tyr Pro Ser Asp Ile Ala Val Glu Trp Glu
```

```
            435                 440                 445
Ser Asn Gly Gln Pro Glu Asn Asn Tyr Lys Thr Thr Pro Val Leu
450                 455                 460

Asp Ser Asp Gly Ser Phe Phe Leu Tyr Ser Lys Leu Thr Val Asp Lys
465                 470                 475                 480

Ser Arg Trp Gln Gln Gly Asn Val Phe Ser Cys Ser Val Met His Glu
                    485                 490                 495

Ala Leu His Asn His Tyr Thr Gln Lys Ser Leu Ser Leu Ser Pro Gly
                500                 505                 510

Lys

<210> SEQ ID NO 19
<211> LENGTH: 488
<212> TYPE: PRT
<213> ORGANISM: Artificial Sequence
<220> FEATURE:
<223> OTHER INFORMATION: A/Anhui/1/2005(H5N1) HA1(+28-259)-Fd-hFc fusion
      protein

<400> SEQUENCE: 19

His Ala Gln Asp Ile Leu Glu Lys Thr His Asn Gly Lys Leu Cys Asp
1               5                   10                  15

Leu Asp Gly Val Lys Pro Leu Ile Leu Arg Asp Cys Ser Val Ala Gly
                20                  25                  30

Trp Leu Leu Gly Asn Pro Met Cys Asp Glu Phe Ile Asn Val Pro Glu
            35                  40                  45

Trp Ser Tyr Ile Val Glu Lys Ala Asn Pro Ala Asn Asp Leu Cys Tyr
50                  55                  60

Pro Gly Asn Phe Asn Asp Tyr Glu Glu Leu Lys His Leu Leu Ser Arg
65                  70                  75                  80

Ile Asn His Phe Glu Lys Ile Gln Ile Ile Pro Lys Ser Ser Trp Ser
                85                  90                  95

Asp His Glu Ala Ser Ser Gly Val Ser Ser Ala Cys Pro Tyr Gln Gly
            100                 105                 110

Thr Pro Ser Phe Phe Arg Asn Val Val Trp Leu Ile Lys Lys Asn Asn
        115                 120                 125

Thr Tyr Pro Thr Ile Lys Arg Ser Tyr Asn Asn Thr Asn Gln Glu Asp
130                 135                 140

Leu Leu Ile Leu Trp Gly Ile His His Ser Asn Asp Ala Ala Glu Gln
145                 150                 155                 160

Thr Lys Leu Tyr Gln Asn Pro Thr Thr Tyr Ile Ser Val Gly Thr Ser
                165                 170                 175

Thr Leu Asn Gln Arg Leu Val Pro Lys Ile Ala Thr Arg Ser Lys Val
            180                 185                 190

Asn Gly Gln Asn Gly Arg Met Asp Phe Phe Trp Thr Ile Leu Lys Pro
        195                 200                 205

Asn Asp Ala Ile Asn Phe Glu Ser Asn Gly Asn Phe Ile Ala Pro Glu
210                 215                 220

Tyr Ala Tyr Lys Ile Val Lys Lys Gly Tyr Ile Pro Glu Ala Pro Arg
225                 230                 235                 240

Asp Gly Gln Ala Tyr Val Arg Lys Asp Gly Glu Trp Val Leu Leu Ser
                245                 250                 255

Thr Phe Leu Arg Ser Asp Lys Thr His Thr Cys Pro Pro Cys Pro Ala
            260                 265                 270

Pro Glu Leu Leu Gly Gly Pro Ser Val Phe Leu Phe Pro Pro Lys Pro
```

```
                275                 280                 285
Lys Asp Thr Leu Met Ile Ser Arg Thr Pro Glu Val Thr Cys Val Val
290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Ala
        355                 360                 365

Leu Pro Ala Pro Ile Glu Lys Thr Ile Ser Lys Ala Lys Gly Gln Pro
370                 375                 380

Arg Glu Pro Gln Val Tyr Thr Leu Pro Pro Ser Arg Glu Glu Met Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Phe Leu Tyr
        435                 440                 445

Ser Lys Leu Thr Val Asp Lys Ser Arg Trp Gln Gln Gly Asn Val Phe
450                 455                 460

Ser Cys Ser Val Met His Glu Ala Leu His Asn His Tyr Thr Gln Lys
465                 470                 475                 480

Ser Leu Ser Leu Ser Pro Gly Lys
                485

<210> SEQ ID NO 20
<211> LENGTH: 471
<212> TYPE: PRT
<213> ORGANISM: Artificial Sequence
<220> FEATURE:
<223> OTHER INFORMATION: A/Anhui/1/2005(H5N1) HA1(+45-259)-Fd-hFc fusion
      protein

<400> SEQUENCE: 20

Asp Gly Val Lys Pro Leu Ile Leu Arg Asp Cys Ser Val Ala Gly Trp
1               5                   10                  15

Leu Leu Gly Asn Pro Met Cys Asp Glu Phe Ile Asn Val Pro Glu Trp
            20                  25                  30

Ser Tyr Ile Val Glu Lys Ala Asn Pro Ala Asn Asp Leu Cys Tyr Pro
        35                  40                  45

Gly Asn Phe Asn Asp Tyr Glu Glu Leu Lys His Leu Leu Ser Arg Ile
    50                  55                  60

Asn His Phe Glu Lys Ile Gln Ile Ile Pro Lys Ser Ser Trp Ser Asp
65                  70                  75                  80

His Glu Ala Ser Ser Gly Val Ser Ser Ala Cys Pro Tyr Gln Gly Thr
                85                  90                  95

Pro Ser Phe Phe Arg Asn Val Val Trp Leu Ile Lys Lys Asn Asn Thr
            100                 105                 110

Tyr Pro Thr Ile Lys Arg Ser Tyr Asn Asn Thr Asn Gln Glu Asp Leu
        115                 120                 125

Leu Ile Leu Trp Gly Ile His His Ser Asn Asp Ala Ala Glu Gln Thr
    130                 135                 140
```

```
Lys Leu Tyr Gln Asn Pro Thr Thr Tyr Ile Ser Val Gly Thr Ser Thr
145                 150                 155                 160

Leu Asn Gln Arg Leu Val Pro Lys Ile Ala Thr Arg Ser Lys Val Asn
            165                 170                 175

Gly Gln Asn Gly Arg Met Asp Phe Phe Trp Thr Ile Leu Lys Pro Asn
        180                 185                 190

Asp Ala Ile Asn Phe Glu Ser Asn Gly Asn Phe Ile Ala Pro Glu Tyr
    195                 200                 205

Ala Tyr Lys Ile Val Lys Lys Gly Tyr Ile Pro Glu Ala Pro Arg Asp
210                 215                 220

Gly Gln Ala Tyr Val Arg Lys Asp Gly Glu Trp Val Leu Leu Ser Thr
225                 230                 235                 240

Phe Leu Arg Ser Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 21
<211> LENGTH: 444
<212> TYPE: PRT
<213> ORGANISM: Artificial Sequence
<220> FEATURE:
<223> OTHER INFORMATION: A/Anhui/1/2005(H5N1) HA1(+72-259)-Fd-hFc fusion
      protein

<400> SEQUENCE: 21

Asn Val Pro Glu Trp Ser Tyr Ile Val Glu Lys Ala Asn Pro Ala Asn
1               5                   10                  15

Asp Leu Cys Tyr Pro Gly Asn Phe Asn Asp Tyr Glu Glu Leu Lys His
            20                  25                  30
```

```
Leu Leu Ser Arg Ile Asn His Phe Glu Lys Ile Gln Ile Ile Pro Lys
            35                  40                  45

Ser Ser Trp Ser Asp His Glu Ala Ser Ser Gly Val Ser Ser Ala Cys
 50                  55                  60

Pro Tyr Gln Gly Thr Pro Ser Phe Phe Arg Asn Val Val Trp Leu Ile
 65                  70                  75                  80

Lys Lys Asn Asn Thr Tyr Pro Thr Ile Lys Arg Ser Tyr Asn Asn Thr
                 85                  90                  95

Asn Gln Glu Asp Leu Leu Ile Leu Trp Gly Ile His His Ser Asn Asp
                100                 105                 110

Ala Ala Glu Gln Thr Lys Leu Tyr Gln Asn Pro Thr Thr Tyr Ile Ser
                115                 120                 125

Val Gly Thr Ser Thr Leu Asn Gln Arg Leu Val Pro Lys Ile Ala Thr
130                 135                 140

Arg Ser Lys Val Asn Gly Gln Asn Gly Arg Met Asp Phe Phe Trp Thr
145                 150                 155                 160

Ile Leu Lys Pro Asn Asp Ala Ile Asn Phe Glu Ser Asn Gly Asn Phe
                165                 170                 175

Ile Ala Pro Glu Tyr Ala Tyr Lys Ile Val Lys Lys Gly Tyr Ile Pro
                180                 185                 190

Glu Ala Pro Arg Asp Gly Gln Ala Tyr Val Arg Lys Asp Gly Glu Trp
                195                 200                 205

Val Leu Leu Ser Thr Phe Leu Arg Ser Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
                260                 265                 270

Asn Trp Tyr Val Asp Gly Val Glu Val His Asn Ala Lys Thr Lys Pro
                275                 280                 285

Arg Glu Glu Gln Tyr Asn Ser Thr Tyr Arg Val Val Ser Val Leu Thr
                290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
                340                 345                 350

Glu Glu Met Thr Lys Asn Gln Val Ser Leu Thr Cys Leu Val Lys Gly
                355                 360                 365

Phe Tyr Pro Ser Asp Ile Ala Val Glu Trp Glu Ser Asn Gly Gln Pro
                370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly Lys
                435                 440
```

<210> SEQ ID NO 22
<211> LENGTH: 300
<212> TYPE: PRT
<213> ORGANISM: Artificial Sequence
<220> FEATURE:
<223> OTHER INFORMATION: A/Anhui/1/2005(H5N1) HA1(+72-115)-Fd-hFc fusion protein

<400> SEQUENCE: 22

```
Asn Val Pro Glu Trp Ser Tyr Ile Val Glu Lys Ala Asn Pro Ala Asn
1               5                   10                  15

Asp Leu Cys Tyr Pro Gly Asn Phe Asn Asp Tyr Glu Glu Leu Lys His
            20                  25                  30

Leu Leu Ser Arg Ile Asn His Phe Glu Lys Ile Gln Gly Tyr Ile Pro
        35                  40                  45

Glu Ala Pro Arg Asp Gly Gln Ala Tyr Val Arg Lys Asp Gly Glu Trp
    50                  55                  60

Val Leu Leu Ser Thr Phe Leu Arg Ser Asp Lys Thr His Thr Cys Pro
65                  70                  75                  80

Pro Cys Pro Ala Pro Glu Leu Leu Gly Gly Pro Ser Val Phe Leu Phe
                85                  90                  95

Pro Pro Lys Pro Lys Asp Thr Leu Met Ile Ser Arg Thr Pro Glu Val
            100                 105                 110

Thr Cys Val Val Val Asp Val Ser His Glu Asp Pro Glu Val Lys Phe
        115                 120                 125

Asn Trp Tyr Val Asp Gly Val Glu Val His Asn Ala Lys Thr Lys Pro
    130                 135                 140

Arg Glu Glu Gln Tyr Asn Ser Thr Tyr Arg Val Val Ser Val Leu Thr
145                 150                 155                 160

Val Leu His Gln Asp Trp Leu Asn Gly Lys Glu Tyr Lys Cys Lys Val
                165                 170                 175

Ser Asn Lys Ala Leu Pro Ala Pro Ile Glu Lys Thr Ile Ser Lys Ala
            180                 185                 190

Lys Gly Gln Pro Arg Glu Pro Gln Val Tyr Thr Leu Pro Pro Ser Arg
        195                 200                 205

Glu Glu Met Thr Lys Asn Gln Val Ser Leu Thr Cys Leu Val Lys Gly
    210                 215                 220

Phe Tyr Pro Ser Asp Ile Ala Val Glu Trp Glu Ser Asn Gly Gln Pro
225                 230                 235                 240

Glu Asn Asn Tyr Lys Thr Thr Pro Pro Val Leu Asp Ser Asp Gly Ser
                245                 250                 255

Phe Phe Leu Tyr Ser Lys Leu Thr Val Asp Lys Ser Arg Trp Gln Gln
            260                 265                 270

Gly Asn Val Phe Ser Cys Ser Val Met His Glu Ala Leu His Asn His
        275                 280                 285

Tyr Thr Gln Lys Ser Leu Ser Leu Ser Pro Gly Lys
    290                 295                 300
```